(12) United States Patent
Gonsalves et al.

(10) Patent No.: US 11,322,048 B2
(45) Date of Patent: May 3, 2022

(54) ULTRASOUND-GUIDED MEDICAL TOOL INSERTION SIMULATORS

(71) Applicant: University of Florida Research Foundation, Incorporated, Gainesville, FL (US)

(72) Inventors: Drew B. Gonsalves, Gainesville, FL (US); David E. Lizdas, Gainesville, FL (US); Samsun Lampotang, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 378 days.

(21) Appl. No.: 15/921,529

(22) Filed: Mar. 14, 2018

(65) Prior Publication Data

US 2018/0225992 A1 Aug. 9, 2018

Related U.S. Application Data

(63) Continuation-in-part of application No. PCT/US2016/051899, filed on Sep. 15, 2016, and a
(Continued)

(51) Int. Cl.
*G09B 23/00* (2006.01)
*G09B 23/28* (2006.01)
(Continued)

(52) U.S. Cl.
CPC ......... *G09B 23/285* (2013.01); *G09B 5/02* (2013.01); *G09B 23/28* (2013.01); *A61B 8/0841* (2013.01); *A61B 8/4254* (2013.01)

(58) Field of Classification Search
CPC .... G09B 23/285; G09B 23/28; G09B 23/286; G09B 23/30; G09B 23/288; G09B 23/303; G09B 23/306; G09B 23/32; G09B 23/34
(Continued)

(56) References Cited

U.S. PATENT DOCUMENTS 6,338,716 B1  1/2002  Hossack et al.
2009/0305213 A1* 12/2009  Burgkart ............ G09B 23/285
                                                  434/267
(Continued)

FOREIGN PATENT DOCUMENTS

EP        2 784 766 A1     10/2014
WO   WO 2014/128301 A1      8/2014
WO   WO 2016/123144 A2      8/2016

OTHER PUBLICATIONS

International Search Report and Written Opinion for International Application No. PCT/US2016/051904 dated Dec. 1, 2016.
(Continued)

*Primary Examiner* — James B Hull
(74) *Attorney, Agent, or Firm* — Wolf, Greenfield & Sacks, P.C.

(57) ABSTRACT

A medical tool insertion simulation apparatus. The medical tool insertion simulation apparatus may comprise a syringe having an injection end, and an elongated member protruding from the injection end of the syringe. The elongated member may be configured to decrease a length of protrusion of the elongated member from the injection end of the syringe. The elongated member may be configured to receive at least one first sensor configured to indicate position information relating to the elongated member. At least one computer-readable storage medium encoded with executable instructions that, when executed by at least one
(Continued)

processor, cause the at least one processor to perform a method for simulating medical tool insertion. A medical tool insertion simulation system.

15 Claims, 16 Drawing Sheets

Related U.S. Application Data continuation-in-part of application No. PCT/US2016/051904, filed on Sep. 15, 2016.

(60) Provisional application No. 62/219,045, filed on Sep. 15, 2015, provisional application No. 62/219,050, filed on Sep. 15, 2015.

(51) Int. Cl.
*G09B 5/02* (2006.01)
*A61B 8/08* (2006.01)
*A61B 8/00* (2006.01)

(58) Field of Classification Search
USPC .................................................. 434/262
See application file for complete search history.

(56) References Cited

U.S. PATENT DOCUMENTS

| | | | | |
|---|---|---|---|---|
| 2012/0189998 A1* | 7/2012 | Kruecker | ............. | G09B 23/286 434/272 |
| 2012/0280988 A1* | 11/2012 | Lampotang | ............. | G06T 19/20 345/419 |
| 2013/0135312 A1 | 5/2013 | Yang et al. | | |
| 2013/0323700 A1* | 12/2013 | Samosky | ............... | G09B 23/28 434/262 |
| 2014/0046261 A1* | 2/2014 | Newman | ................ | A61B 5/062 604/158 |
| 2014/0120505 A1* | 5/2014 | Rios | ....................... | G09B 23/30 434/219 |
| 2014/0134586 A1* | 5/2014 | Stein | .................... | G09B 23/286 434/262 |
| 2014/0257080 A1 | 9/2014 | Dunbar et al. | | |
| 2015/0056591 A1* | 2/2015 | Tepper | ................. | G09B 23/286 434/262 |
| 2015/0084897 A1 | 3/2015 | Nataneli et al. | | |
| 2016/0081653 A1* | 3/2016 | Masuda | ............... | A61B 8/4254 600/424 |
| 2016/0104393 A1* | 4/2016 | Savitsky | .............. | G09B 23/285 434/262 |
| 2016/0314715 A1* | 10/2016 | Savitsky | .............. | A61B 8/4254 |
| 2017/0196535 A1* | 7/2017 | Arai | ................... | A61B 18/1477 |
| 2018/0211567 A1* | 7/2018 | Pfeifer | ................... | G01D 5/165 |
| 2018/0336803 A1* | 11/2018 | Patil | ...................... | A61B 8/4254 |
| 2021/0043112 A1* | 2/2021 | Miller | .................. | G09B 23/303 |

OTHER PUBLICATIONS

International Preliminary Report on Patentability for International Application No. PCT/US2016/051904 dated Mar. 29, 2018.
International Search Report and Written Opinion for International Application No. PCT/US2016/051899 dated Feb. 7, 2017.
International Preliminary Report on Patentability for International Application No. PCT/US2016/051899 dated Mar. 29, 2018.

* cited by examiner

ULTRASOUND-GUIDED MEDICAL TOOL INSERTION SIMULATORS

RELATED APPLICATIONS

This application is a continuation-in-part of International Application No. PCT/US2016/051904, filed on Sep. 15, 2016, which claims the benefit under 35 U.S.C. § 119(e) of U.S. Provisional Patent Application Ser. No. 62/219,050, filed on Sep. 15, 2015, entitled "ULTRASOUND-GUIDED MEDICAL TOOL INSERTION SIMULATORS," and this application is a continuation-in-part of International Application No. PCT/US2016/051899, filed on Sep. 15, 2016, which claims the benefit under 35 U.S.C. § 119(e) of U.S. Provisional Patent Application Ser. No. 62/219,045, filed on Sep. 15, 2015, entitled "ULTRASOUND-GUIDED MEDICAL TOOL INSERTION SIMULATORS," each of which is hereby incorporated herein by reference in its entirety.

BACKGROUND

A simulation provides representations of certain key characteristics or behaviors of a selected physical or abstract system. Simulations can be used to show the effects of particular courses of action. A physical simulation is a simulation in which physical objects are substituted for a real thing or entity. Physical simulations are often used in interactive simulations involving a human operator for educational and/or training purposes. For example, mannequin patient simulators are used in the healthcare field, flight simulators and driving simulators are used in various industries, and tank simulators may be used in military training.

Physical simulations or objects provide a real tactile and haptic feedback for a human operator and a 3-dimensional (3D) interaction perspective suited for learning psycho-motor and spatial skills. In the health care industry, as an example, medical simulators are being developed to teach therapeutic and diagnostic procedures, medical concepts, and decision making skills. Many medical simulators involve a computer or processor connected to a physical representation of a patient, such as a mannequin patient simulator.

Virtual simulations have also been used for education and training. Typically, the simulation model is instantiated via a display such as a computer, PDA, or cell phone screen; or a stereoscopic, 3D, holographic, or panoramic display. An intermediary device, often a mouse or joystick, may be needed to interact with the simulation.

The use of ultrasound in medicine is becoming the standard of care for many procedures. Procedures that utilize ultrasound range from fetal imaging to the safe insertion and guidance of a needle inside a patient. Ultrasound uses sound waves to generate a 2-dimensional (2D) (or in some machines, a 3D) image of underlying muscle, tissue, bone, and other structures.

SUMMARY

Some aspects include a medical tool insertion simulation apparatus. The medical tool insertion simulation apparatus may comprise a syringe having an injection end, and an elongated member protruding from the injection end of the syringe. The elongated member may be configured to decrease a length of protrusion of the elongated member from the injection end of the syringe. The elongated member may be configured to receive at least one first sensor configured to indicate position information relating to the elongated member.

Further aspects include at least one computer-readable storage medium encoded with executable instructions that, when executed by at least one processor, cause the at least one processor to perform a method for simulating medical tool insertion. The method may comprise: receiving ultrasound data representing an object being imaged; receiving position data from a hand-held device; computing a position of a medical tool simulator attached to the hand-held device; and generating an image of the object with an image of a simulated medical tool positioned relative to the object based on the computed position of the medical tool simulator.

Additional aspects include a medical tool insertion simulation system. The medical tool insertion simulation system may comprise a medical tool simulator configured to decrease a length of protrusion of a protruding member of the medical tool simulator; and an ultrasound probe. The medical tool simulator may be configured to receive at least one first sensor. The ultrasound probe may be configured to receive at least one second sensor. The at least one first sensor and/or the at least one second sensor may be configured to indicate a relative position between the medical tool simulator and the ultrasound probe.

Further aspects include at least one computer-readable storage medium encoded with executable instructions that, when executed by at least one processor, cause the at least one processor to perform a method for simulating medical tool insertion. The method may comprise: presenting a user interface representing a simulated medical tool on a display of the first device; receiving, from a first sensor of the first device, an orientation of the first device; and transmitting, to a second device, the orientation of the first device.

In some embodiments, the method may further comprise: receiving, via the user interface, a sliding user input representing a depth of insertion of the simulated medical tool; and transmitting, to the second device, the sliding user input. Alternatively or additionally, the method may further comprise: receiving, from a second sensor of the first device, a position and/or an orientation of a tracking element configured to be attached to an ultrasound probe. In some embodiments, the second sensor may comprise a magnetometer, and the tracking element may comprise a magnet.

In some embodiments, the method may further comprise: receiving, from a second sensor of the first device, at least one image of an environment of the first device; and determining a position and/or an orientation of an ultrasound probe based on the at least one image of the environment of the first device.

In some embodiments, the first sensor may comprise a gyroscope. Alternatively or additionally, the method may further comprise: receiving, via a user control, a calibration of the first sensor of the first device.

Further aspects include a display device for simulated medical tool insertion based on information received from a mobile device for use as a medical tool simulator. The display device may comprise at least one processor configured to: receive, from the mobile device, an orientation of the mobile device; compute, based on the orientation of the mobile device, an orientation of a simulated medical tool; and display one or more ultrasound images including an overlay indicating in real-time the orientation of the simulated medical tool.

In some embodiments, the at least one processor may be further configured to receive, from the mobile device, a first user input representing a depth of movement of the simulated medical tool, and the at least one processor may be configured to display the one or more ultrasound images at least by displaying the one or more ultrasound images including the overlay indicating in real-time the at least one of the orientation of the simulated medical tool and the first user input.

In some embodiments, the at least one processor may be further configured to: receive, from the mobile device, data indicating a relative position of the mobile device and an ultrasound probe. Additionally, the at least one processor may be further configured to: receive, from the mobile device, a position and/or an orientation of a tracking element configured to be attached to the ultrasound probe, wherein the overlay may further indicate in real-time at least one of the position of the tracking element and the orientation of the tracking element. Additionally, the at least one processor may be further configured to: receive, from the mobile device, a position of the ultrasound probe and/or an orientation of the ultrasound probe, wherein the overlay may further indicate in real-time at least one of the position of the ultrasound probe and the orientation of the ultrasound probe.

In some embodiments, the at least one processor may be further configured to: receive, from an ultrasound probe, ultrasound data; and display the one or more ultrasound images based on the ultrasound data. Alternatively or additionally, the at least one processor may be further configured to: receive, from a camera, at least one original ultrasound image captured by the camera; and display the one or more ultrasound images based on the at least one original ultrasound image. Additionally, the at least one processor may be further configured to: receive, via a user interface of the display device, a second user input; and define, based on the second user input, an area of capture for the camera.

In some embodiments, the one or more ultrasound images may comprise live ultrasound images. Alternatively or additionally, the one or more ultrasound images may comprise prerecorded ultrasound images.

In some embodiments, the at least one processor may be further configured to: compute the one or more ultrasound images based on prerecorded ultrasound images and an orientation of an ultrasound probe.

Additional aspects include a method of simulating a medical procedure. The method may comprise receiving information from a mobile device configured with an application to simulate a medical tool and to transmit orientation information; receiving ultrasound image data from an ultrasound probe; and computing an image of an object with an image of a simulation oriented relative to the object based on the received information.

In some embodiments, computing the image may be based on an assumption that the mobile device has a known position relative to the ultrasound probe.

DETAILED DESCRIPTION

Figure 2:
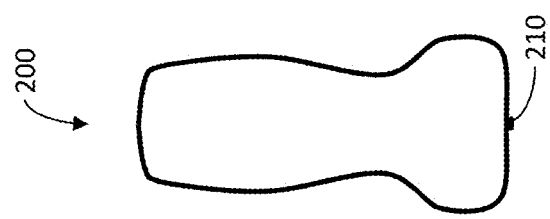
FIG. 2 is a diagram of an exemplary ultrasound probe according to some embodiments.

The inventors have recognized and appreciated that more realistic, applicable, and accessible simulations of ultrasound-guided needle insertion (and, therein, simulations of ultrasound usage itself) may be particularly valuable because improper use of ultrasound and lack of knowledge can increase the number of needle passes and movement inside a patient. Increased passes and internal movement of a needle may put the patient at risk for mild complications, such as discomfort, as well as more serious complications, like a pneumothorax. Moreover, improper use of or inexperience with ultrasound alone may cause additional discomfort, inconvenience, and/or expense by prolonging the time the patient must endure the potentially invasive procedure and the clinical visit.

The inventors have recognized and appreciated that a more realistic ultrasound-guided needle insertion simulation may be provided using an actual living person as a subject rather than an inanimate object. Indeed, using a living person for the simulation may greatly improve the learning experience for the user. Practicing needle insertion on an inanimate object may not provide a learning experience equivalent to using a living person. For example, a living person may require a "bed-side manner," may move at inopportune times, will at least move due to breathing, may respond to the user in ways that are not easily simulated by an inanimate object or even an animal, and so on.

The inventors have recognized and appreciated that a more realistic and applicable ultrasound-guided needle insertion simulation may also be provided using actual, live ultrasound images. Actual, live ultrasound images may provide more information and more variety of experience than, for example, prerecorded ultrasound images. Moreover, actual, live ultrasound images may allow the user to account for anatomical differences and anomalies between individual people, which may require important adjustments to be made for a successful needle insertion or practice procedure. The actual, live ultrasound images may also allow the user to overcome such anatomical differences or anomalies. In contrast, many current simulators reference a library of pre-scanned and recorded (or graphically modeled) ultrasound images (which may originate from a single scanned subject) or use real ultrasound machines to scan objects that are not actually the subject of the injection. Such "fictitious" ultrasound images are not as realistic as actual, live ultrasound images and cannot account for anatomical differences and anomalies, although prerecorded ultrasound images may still be useful in some embodiments herein. For example, a simulation using prerecorded ultrasound images may be less expensive than a system requiring actual, functioning ultrasound equipment.

The inventors have recognized and appreciated that a more realistic and applicable ultrasound-guided needle insertion simulation may be provided by using an actual patient in the simulation immediately before the actual procedure on that same patient (in other words, in a "just-in-time" setting). For example, needle insertion can be very difficult to perform in general, and the variation in anatomy between different patients (even when subtle) can increase the difficulty significantly. A clinician may struggle to find a vein or avoid areas or organs that the needle should not contact or enter, or may struggle to perform the operation well on one patient after having trained on a different subject (either via simulation or actual procedures). This difficulty can create significant discomfort and pain for the patient as well as unnecessary puncture wounds and bleeding or even more severe conditions, such as a pneumothorax. The inventors have recognized and appreciated that practicing the needle insertion using the actual patient immediately before performing the actual insertion may enable the clinician to more skillfully perform the procedure. For example, the clinician may use the simulated insertion to become familiar with the patient's unique anatomy and learn the precise position and orientation that the syringe should have to maximize the probability of a successful insertion. A clinician may practice the exact same needle passes just before placing a real needle inside a real patient. For example, if a clinician were getting ready to start an intravenous line on a patient, he or she could simulate the procedure on the patient in the same location on the arm.

The inventors have recognized and appreciated that a more realistic and applicable ultrasound-guided needle insertion simulation may also be provided by tracking the orientation and/or position of a needle simulator (which may be a physical object or device that is used in place of an actual syringe and needle). For example, tracking the orientation of a needle simulator may provide a simulation system with basic information needed to represent to the user how well the simulated needle insertion is proceeding. One way in which this representation may be performed is through display of an image representing the needle simulator from a perspective not visible to the user. As the user can only see the needle simulator from the perspective of his or her own eyes, for example, the user cannot see where the needle simulator would be going inside a subject if the needle simulator were an actual needle. By tracking the orientation and/or position of the needle simulator and displaying an image of the inside of the subject with some representation of the needle simulator (such as an overlay in the shape of an actual needle) so that its simulated position inside the subject (if it were an actual needle) is apparent, the simulation can represent to the user how well the simulated needle insertion is proceeding. The image or images of the inside of the subject may be actual, live ultrasound images (or prerecorded images, in some embodiments), as discussed herein. Therefore, without actually puncturing the subject's skin, the user may see where an actual needle would go inside the subject if placed in the same orientation and position as the needle simulator. Moreover, the simulated needle insertion may more closely simulate an actual ultrasound-guided needle insertion, in which a user would see an actual needle inside the subject in ultrasound images during the insertion. It should be appreciated that a needle simulator may be a type of medical tool simulator.

The inventors have recognized and appreciated that a more realistic and applicable ultrasound-guided needle insertion simulation may also be provided by using magnetic tracking. For example, magnetic tracking can determine the positions of object, or at least their relative positions, with sub-millimeter precision. Moreover, magnetic tracking can function without requiring specific orientations and/or positions so that some degree of line-of-sight is available, as optical sensors require. For example, optical sensors may be easily and accidentally blocked during a needle insertion simulation, and their usability in such situations may be severely impaired or non-existent. Magnetic sensors, on the other hand, may provide the same usability regardless of their orientation, position, or obstructions. Moreover, magnetic sensors may provide higher precision than optical sensors for comparable price-points. Additionally, commercially available magnetic sensors may be used, which may reduce the complexity and cost of the simulation system.

The inventors have recognized and appreciated that a more accessible ultrasound-guided needle insertion simulation may be provided in a training or learning setting (such as a classroom) as well as a clinical setting. For example, even without variation in anatomy between different patients, needle insertion can be a very difficult procedure to learn. A clinician may need to practice many times before being able to perform needle insertion (even with guidance from ultrasound) in a way that is as fast, comfortable, and painless as possible for the patient. Numerous practice insertions may allow the clinician to develop muscle memory that may be useful in all needle insertions.

The inventors have recognized and appreciated that a more accessible ultrasound-guided needle insertion simulation may be provided using a device already in the possession of many consumers as a virtual needle or needle emulator. In some embodiments, a simulation may take advantage of a complex, capable mobile device that is commonly in the possession of many potential users, such as clinical students. For example, a smartphone or other mobile device (which may not necessarily have a cellular connection) may be used as a virtual needle by configuring the mobile device with appropriate software (and, optionally, hardware). Using such mobile devices may reduce the cost of training due to the elimination of at least one item to rent or purchase. Moreover, using such mobile devices may reduce the learning curve of users, as they may already be familiar with the interface of the mobile devices, which may be used directly in the simulation.

The inventors have recognized and appreciated that a highly realistic ultrasound-guided needle insertion simulation may be provided by using a device that shares many or most physical characteristics with an actual syringe and needle. For example, in some embodiments, an actual syringe may be fitted with a retractable "needle," which may actually be an elongated member not made to puncture, with appropriate dimensions to take the place of an actual needle within a syringe. Alternatively, a customized or modified syringe may be used with an included elongated member. Matching physical characteristics of an actual syringe and needle, such as dimensions, weight, materials, and so on, may increase the realism, precision, and utility of the simulation. Moreover, using a device that is physically similar to an actual syringe and needle may also provide additional precision by providing more convenient locations for attaching or embedding one or more tracking devices that can be represented realistically to the user, as described below. For example, while a mobile device such as a smartphone may provide a less expensive and more accessible needle simulator, a device that is physically similar to a syringe and needle may be able to support a tracking device more easily, and any representation of the tracking to the user may show syringe and needle-shaped objects in a way that is faithful to the actual structure of the device.

It should be appreciated that embodiments and techniques herein may alternatively or additionally be used for any invasive procedure inside a subject's body and are not limited to ultrasound-guided needle insertion. For example, rather than a needle, any invasive medical tool may be simulated, and rather than ultrasound, any suitable guidance system may be used.

It should also be appreciated that any embodiments or techniques described in one exemplary implementation herein may be used in combination with or as a replacement for any embodiments or techniques described in another exemplary implementation.

According to some embodiments, an ultrasound probe may be used to image (or pretend to image) a portion of an object (e.g., a patient or other human subject), and a handheld device (e.g., a tool or a mobile device) may be used to simulate an invasive medical tool (e.g., the device may be made to look like the medical tool and simulate some function of the medical tool). Ultrasound data representing the object may be received from the ultrasound probe. Positional data (e.g., orientation and/or position) may be received from the hand-held device and potentially from the ultrasound probe. The positional data may be used to calculate simulated positional information of the hand-held device or a portion thereof that the medical tool would have if inserted into the object from the orientation and/or position of the hand-held device or a portion thereof. An image of the object with an image of the hand-held device or a portion thereof positioned relative to the object may be generated and displayed.

Exemplary Implementation of the System

Figure 1:
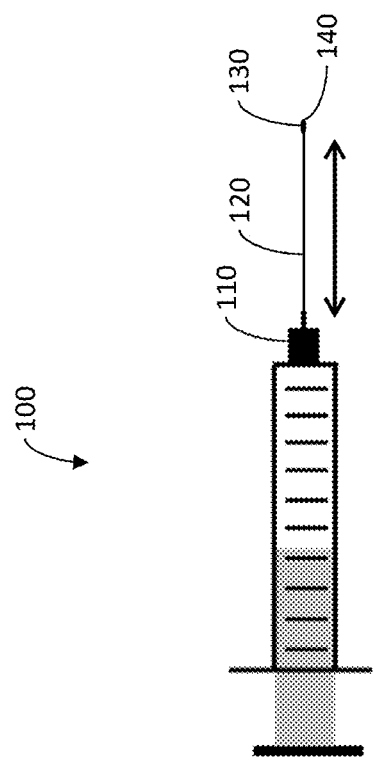
FIG. 1 is a diagram of an exemplary apparatus for needle insertion simulation according to some embodiments.

FIG. 1 illustrates an exemplary apparatus for needle insertion simulation according to some embodiments. In some embodiments, the apparatus may include a syringe 100. Additionally, the syringe 100 may have an injection end 110. The apparatus may also include an elongated member 120 protruding from the injection end 110 of the syringe 100.

According to some embodiments, the elongated member 120 may decrease a length of protrusion of the elongated member 120 from the injection end 110 of the syringe 100. For example, the elongated member 120 may retract into the syringe 100, in the direction from the injection end 110 to the opposite end of the syringe 100, when a threshold force is applied at an end 140 of the elongated member 120. The end 140 at which the threshold force may be applied may be located opposite the syringe 100 when the elongated member 120 is fully protruding from the injection end 110 of the syringe 100.

According to some embodiments, the retraction of the elongated member 120 may occur when the end 140 of the elongated member 120 contacts a surface, such as human skin. For example, when a user begins a simulated needle insertion on a living subject, the elongated member 120 (which may simulate the needle itself) may be pressed against the skin of the subject where the insertion is meant to occur. If the elongated member 120 is pressed against the skin with a force at least as great as the threshold force into the syringe 100, the elongated member 120 may retract into the syringe 100 rather than puncturing the skin. In accordance with some embodiments the elongated member 120 may retract into syringe 100 when it encounters a force that is less than required to puncture a sift surface, such as human skin, against which the elongated member might be pressed in operation. Setting the threshold force may make puncture unlikely. To make puncturing especially unlikely, the end 140 of the elongated member 120 may be flat or rounded rather than pointed, like many actual needles.

According to some embodiments, the syringe 100 or the elongated member 120 may include a spring or any other suitable component (alternatively or additionally, the syringe 100 or the elongated member 120 may be telescoping such that either or both may retract into themselves) that may maintain the elongated member 120 in a position of full protrusion out of the injection end 110 of the syringe 100 except when a threshold force is applied to the end 140 of the elongated member 120. When the threshold force is no longer applied to the end 140 of the elongated member 120, the spring may return the elongated member 120 to the position of full protrusion. For example, when a user is completing a simulated needle insertion, the user may move the syringe 100 away from the skin of the subject such that the force applied to the end 140 of the elongated member 120 into the syringe 100 is less than the threshold force. In response, the elongated member 120 may return to the position of full protrusion.

According to some embodiments, the elongated member 120 may receive or support the attachment of at least one first sensor 130. Additionally, the first sensor 130 may indicate position information relating to the elongated member 120. Alternatively or additionally, the first sensor 130 may indicate an orientation of the elongated member 120. For example, the first sensor 130 may be a magnetic sensor in a magnetic tracking system (e.g., Ascension Flock of Birds), which may provide sub-millimeter tracking precision. Alternatively, the first sensor 130 may be a capacitive sensor, a potentiometer, or any other suitable sensor.

According to some embodiments, the first sensor 130 may be attached to a tip (such as the end 140) of the elongated member 120. Additionally, the first sensor 130 may indicate information based on which another component may detect flexing of the elongated member 120 against another object. For example, the first sensor 130 may indicate the orientation and position of the elongated member 120, based on which flexing may be determined by a magnetic tracking system or any suitable component. For example, if the end 140 of the elongated member 120 is not where expected (e.g., relative to a third sensor or another portion of the elongated member 120) given the orientation of the elongated member 120, this discrepancy may suggest flexing and may provide information needed to calculate a degree of flexing. The magnetic tracking system or other suitable component may process data from the first sensor 130 or another sensor that indicates strain or bending data. Alternatively or additionally, the first sensor 130 may detect flexing directly. For example, the first sensor 130 may detect when the user is pushing the elongated member 120 against the skin of the subject such that flexing occurs. Flexing may be a sign that the user is not performing a simulated insertion along the central axis of the syringe 100 and the elongated member 120.

FIG. 2 illustrates an exemplary ultrasound probe 200 according to some embodiments. In some embodiments, the ultrasound probe 200 may receive or support the attachment of at least one second sensor 210. Additionally, the second sensor 210 may indicate position information relating to the ultrasound probe 200. Alternatively or additionally, the second sensor 210 may indicate an orientation of the ultrasound probe 200.

According to some embodiments, the ultrasound probe 200 may capture one or more images of a portion of an object against which the ultrasound probe 200 is positioned. Additionally, the portion of the object of which images are captured may depend on the orientation and position of the ultrasound probe 200 with respect to the object. For example, rotating or translating the ultrasound probe 200 may cause a different portion of the object to be captured than before the rotation or translation.

Figure 3:
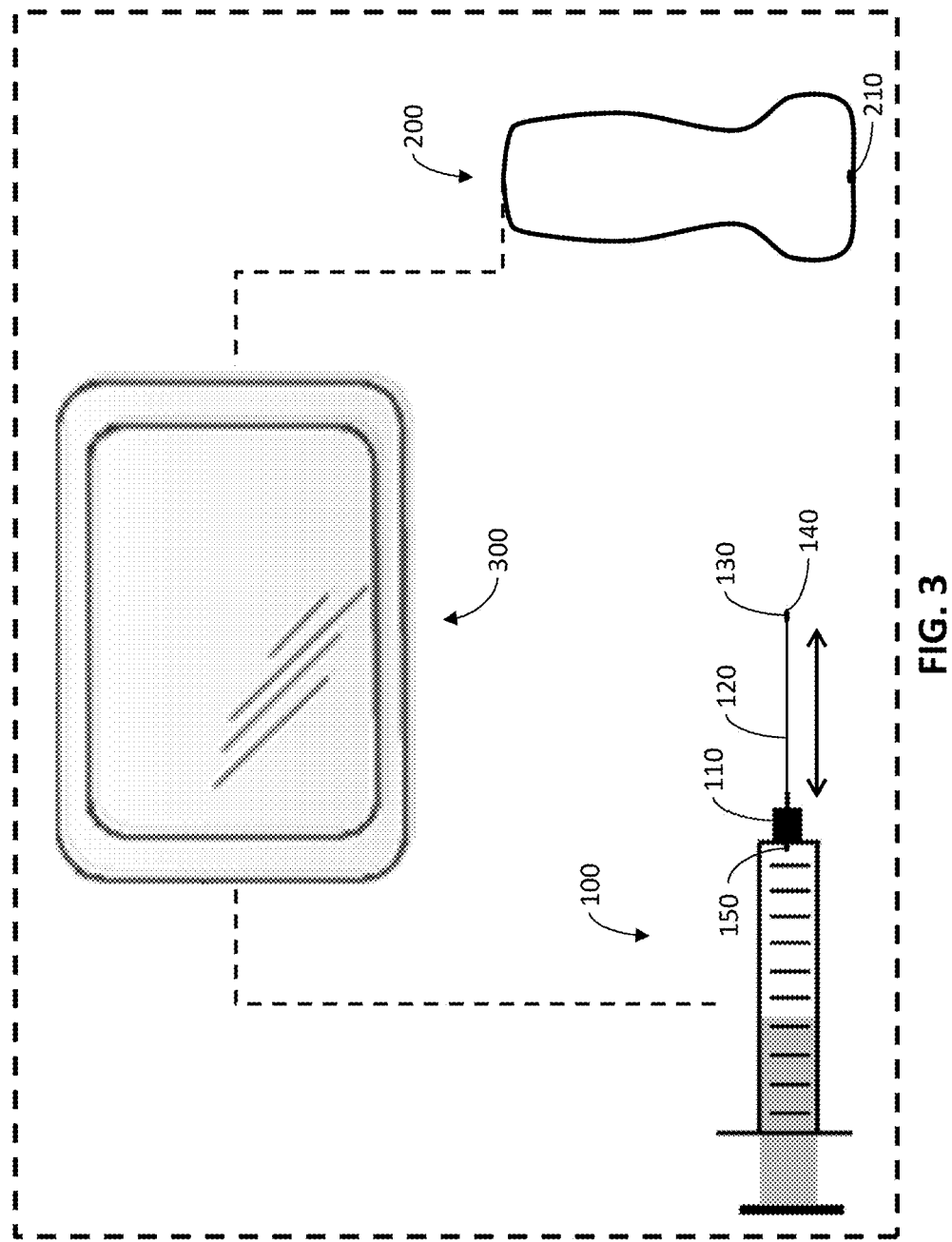
FIG. 3 is a diagram of an exemplary system for needle insertion simulation according to some embodiments.

FIG. 3 illustrates an exemplary system for needle insertion simulation according to some embodiments. In some embodiments, the system may include the syringe 100 and the ultrasound probe 200. The syringe 100 and/or the elongated member 120 may receive or support the attachment of at least one third sensor 150. The third sensor 150 may indicate a relative depth of movement of the elongated member 120 within the syringe 100. For example, the third sensor 150 may indicate the degree of protrusion of the elongated member 120 from the injection end 110 of the syringe 100 or from any other reference point. This information may be used to show how deep inside the subject the elongated member 120 would be if it were an actual needle. In other words, the relative depth may represent motion of the needle (which may be displayed, as described below).

According to some embodiments, the system may include a display device 300. The display device 300 may be an ultrasound machine, a monitor, a television, a desktop or laptop computer, a smartphone, a tablet, and/or any other suitable components. The display device 300 may, in some embodiments, include at least one processor, at least one memory, at least one computer-readable storage medium, and/or any other suitable components. Alternatively or additionally, processing may occur in hardware associated with the display device 300 and/or in other hardware, which may include at least one processor.

In some embodiments, the display device 300 may receive the position of the elongated member 120, the orientation of the elongated member 120, the position of the ultrasound probe 200, and/or the orientation of the ultrasound probe 200. Alternatively, the display device 300 may receive images for display that are generated based on the position of the elongated member 120, the orientation of the elongated member 120, the position of the ultrasound probe 200, and/or the orientation of the ultrasound probe 200. Additionally, the display device 300 may receive, from the ultrasound probe 200, ultrasound data. For example, the ultrasound data may include information needed to generate ultrasound images (and this generation of the ultrasound images may be performed by the display device 300 or by any other suitable device) for display on the display device 300.

According to some embodiments, the display device 300 may register positional information relating to the elongated member 120 and/or the ultrasound probe 200 for use in computing simulated positional information (e.g., a simulated orientation and/or position) of virtual representations of the elongated member 120 and/or the ultrasound probe. For example, the display device 300 may compute a simulated position (based on the positional information) of the elongated member 120 within one or more ultrasound images to be generated from the ultrasound data, which may be used to display ultrasound images with an overlay showing the simulated position of the elongated member 120 (as described below).

According to some embodiments, the display device 300 may display, based on the ultrasound data, one or more ultrasound images. Additionally, the ultrasound images may include an overlay indicating, in real-time, information relating the elongated member 120 with the ultrasound probe 200. Alternatively, the display device 300 may display such an overlay on top of or otherwise in combination with the ultrasound images. For example, the overlay may include a representation or depiction of the elongated member 120, which may be referred to as a simulated needle (which may be a virtual representation of an actual needle, corresponding to the needle simulator). The overlay may be stored or generated based on various sensors, including sensors 130, 150, and 210. It should be appreciated that a simulated needle may be a type of simulated medical tool.

According to some embodiments, the display device 300 (or any other suitable component with processing ability) may compute the information relating the elongated member 120 with the ultrasound probe 200 based on at least one of the following: the position of the elongated member 120, the orientation of the elongated member 120, the relative depth of movement of the elongated member 120 within the syringe 100, the position of the ultrasound probe 200, and the orientation of the ultrasound probe 200. For example, the display device 300 may receive positional information relating to the elongated member 120 and the ultrasound probe 200 as well as ultrasound data, compute a simulated position (based on the positional information) of the elongated member 120 within one or more ultrasound images to be generated from the ultrasound data, and display the ultrasound images with the overlay showing the simulated position of the elongated member 120. The relative depth may be used to simulate what a user would see on ultrasound if a real needle were inserted to the indicated depth while actually performing a procedure.

According to some embodiments, the orientation of the elongated member 120 may include three degrees of freedom, including a yaw, a pitch, and a roll of the elongated member 120. Additionally, the position of the elongated member 120 may include three degrees of freedom, including an X position, a Y position, and a Z position (each corresponding to their respective axes). According to some embodiments, the depth of movement of the elongated member 120 within the syringe 100 may include one degree of freedom.

According to some embodiments, the orientation of the ultrasound probe 200 may include three degrees of freedom, including a yaw, a pitch, and a roll of the ultrasound probe 200. Additionally, the position of the ultrasound probe 200 may include three degrees of freedom, including an X position, a Y position, and a Z position (each corresponding to their respective axes).

According to some embodiments, the ultrasound images may be or at least include live ultrasound images, as discussed herein. Alternatively or additionally, the ultrasound images may be or at least include prerecorded ultrasound images. The advantages of both of these are discussed herein.

According to some embodiments, the first sensor 130, the second sensor 210, and the third sensor 150 may comprise magnetic sensors. The magnetic sensors may be part of a magnetic tracking system such as Ascension Flock of Birds, which may provide sub-millimeter tracking precision. The sensors may be wired (although some sensors may be wireless, as described herein). Alternatively or additionally, these sensors may be capacitive sensors, potentiometers, or any other suitable sensors. For example, the third sensor 150 may be a transducer, such as a linear potentiometer. In some embodiments, positional information from the first sensor 130, the second sensor 210, and/or the third sensor 150 may be used to perform processing for simulating medical tool insertion, as described below.

Figure 4:
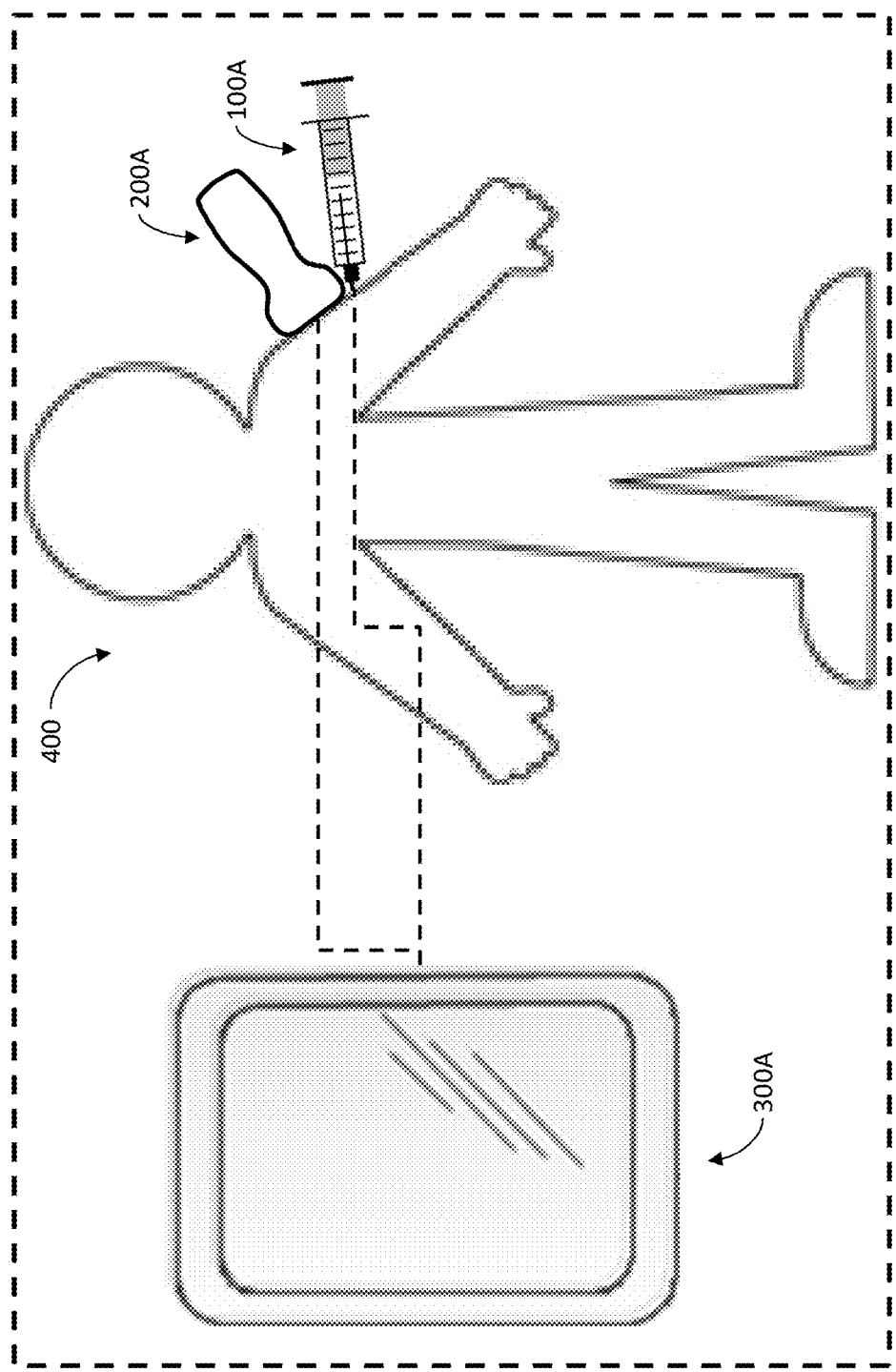
FIG. 4 is a diagram of an exemplary system for needle insertion simulation for use on a subject according to some embodiments.

FIG. 4 illustrates an exemplary system for needle insertion simulation for use on a subject 400 according to some embodiments. In some embodiments, the system may include a needle simulator 100A (which may correspond to the syringe 100). The needle simulator 100A may include a protruding member (which may correspond to a needle being simulated, while the rest of the needle simulator 100A may correspond to a syringe being simulated). The protruding member may shorten or decrease the length of its protrusion (shown inside the needle simulator 100A). For example, the needle simulator 100A may retract the protruding member into the needle simulator when a threshold force is applied at an end of the needle simulator 100A, as described herein. Additionally, the needle simulator 100A may receive or support the attachment of at least one first sensor (which may correspond to first sensor 130) (not shown).

According to some embodiments, the system may include an ultrasound probe 200A (which may correspond to ultrasound probe 200). The ultrasound probe 200A may receive or support the attachment of at least one second sensor (which may correspond to second sensor 210) (not shown). Additionally, the first sensor and/or the second sensor may indicate a relative position between the needle simulator 100A and the ultrasound probe 200A.

According to some embodiments, the first sensor and/or the second sensor may indicate a relative orientation between the needle simulator 100A and the ultrasound probe 200A. Additionally, the needle simulator 100A and/or the protruding member may receive or support the attachment of at least one third sensor (which may correspond to third sensor 150) (not shown) configured to indicate a relative depth of movement of the protruding member within the needle simulator 100A.

According to some embodiments, the system may include a display device 300A (which may correspond to display device 300). The display device 300A may receive the relative position of the needle simulator 100A and the ultrasound probe 200A and/or the relative orientation of the needle simulator 100A and the ultrasound probe 200A. Additionally, the display device 300A may receive, from the ultrasound probe, ultrasound data, and may display, based on the ultrasound data, one or more ultrasound images including an overlay indicating, in real-time, information relating the needle simulator 100A with the ultrasound probe 200A.

According to some embodiments, the ultrasound probe 200A may be placed on the subject 400 in order to provide the ultrasound data received by the display device 300A. Additionally, the needle simulator 100A may be pressed against the subject 400 (typically on the subject's skin, but clothing may also be used for a less realistic simulation) in order to simulate the ultrasound-guided needle insertion. In some embodiments, the display device 300A may show the user (not shown) where the needle simulator 100A would be inside the subject 400 if the needle simulator 100A were an actual needle.

Figure 8:
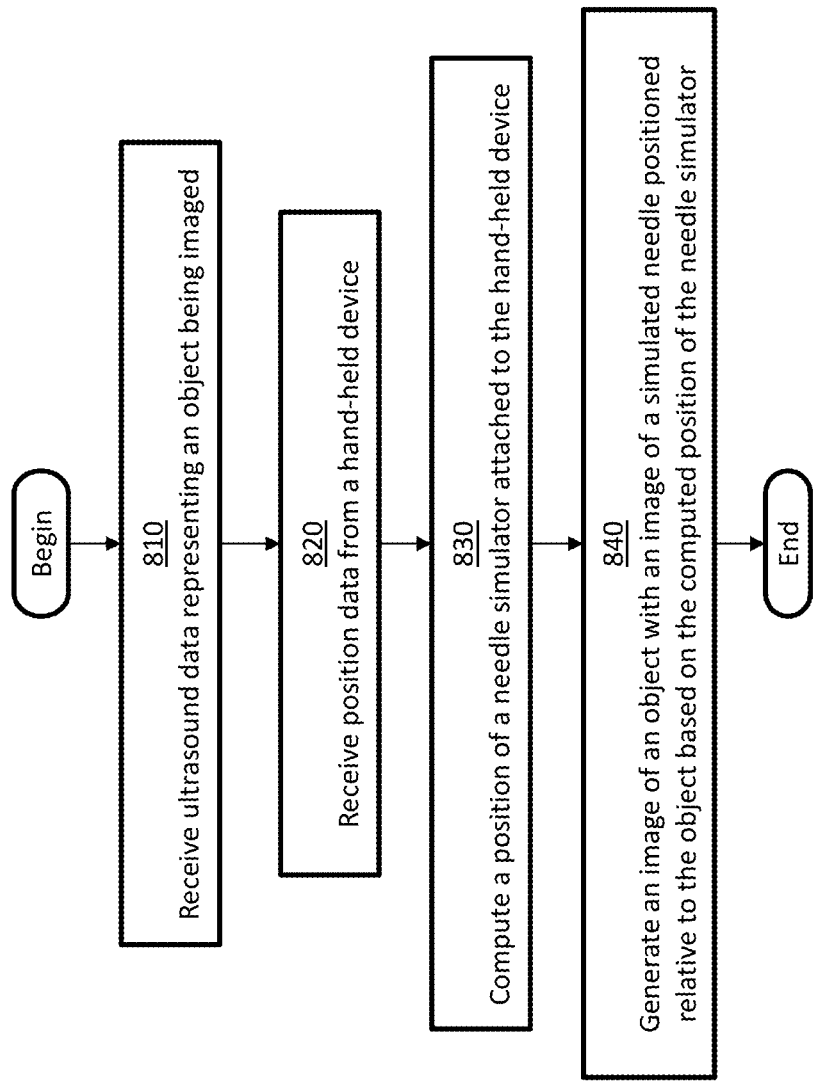
FIG. 8 is a flowchart of a method for simulating needle insertion according to some embodiments.

It should be appreciated from the foregoing that some embodiments are directed to a method for simulating needle insertion, as illustrated in FIG. 8. The method may be performed by at least one processor caused to do so by executing instructions encoded on at least one computer-readable storage medium. The method begins at act 810, at which ultrasound data representing an object (e.g., the subject 400) being imaged may be received. The method then proceeds to act 820, at which position data from or relating to a hand-held device (e.g., the syringe 100) may be received.

The method proceeds then to act 830, at which a position of a needle simulator (e.g., the elongated member 120) attached to the hand-held device may be computed. Then, the method proceeds to act 840, at which an image of the object with an image of a simulated needle positioned relative to the object based on the computed position of the needle simulator may be generated. The method may then end or be repeated for additional stages of a simulation or other simulations. The acts and techniques of this method are described in further detail above.

Figure 9:
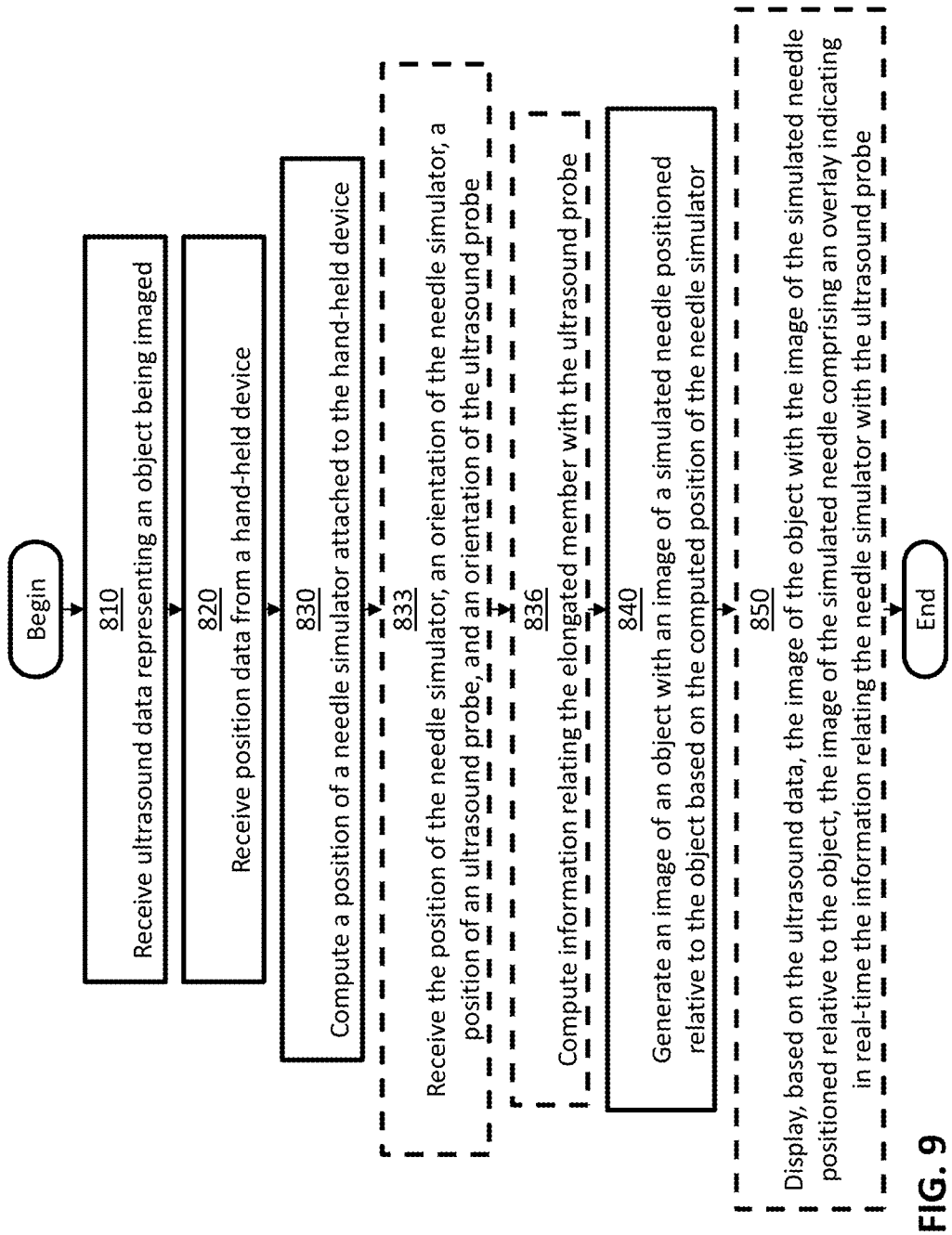
FIG. 9 is a flowchart of an additional method for simulating needle insertion according to some embodiments.

It should be appreciated from the foregoing that some embodiments are directed to an additional method for simulating needle insertion, as illustrated in FIG. 9. The method may be performed by at least one processor caused to do so by executing instructions encoded on at least one computer-readable storage medium. The method begins at act 810 (previously described). The method then proceeds to act 820 (previously described). The method proceeds then to act 830 (previously described). Optionally, the method proceeds to act 833, at which the position of the needle simulator, an orientation of the needle simulator, a position of an ultrasound probe (e.g., ultrasound probe 200), and an orientation of the ultrasound probe may be received.

The method optionally proceeds to act 836, at which information relating the elongated member with the ultrasound probe may be computed based on at least one of the position of the elongated member, the orientation of the elongated member, the relative depth of movement of the elongated member within the syringe, the position of the ultrasound probe, and the orientation of the ultrasound probe. The method proceeds then to act 840 (previously described). Then the method optionally proceeds to act 850, at which the image of the object with the image of the simulated needle positioned relative to the object may be displayed based on the ultrasound data, the image of the simulated needle comprising an overlay indicating in real-time the information relating the needle simulator with the ultrasound probe. The method may then end or be repeated for additional stages of a simulation or other simulations. The acts and techniques of this method are described in further detail above.

Additional Exemplary Implementation of the System

Figure 5:
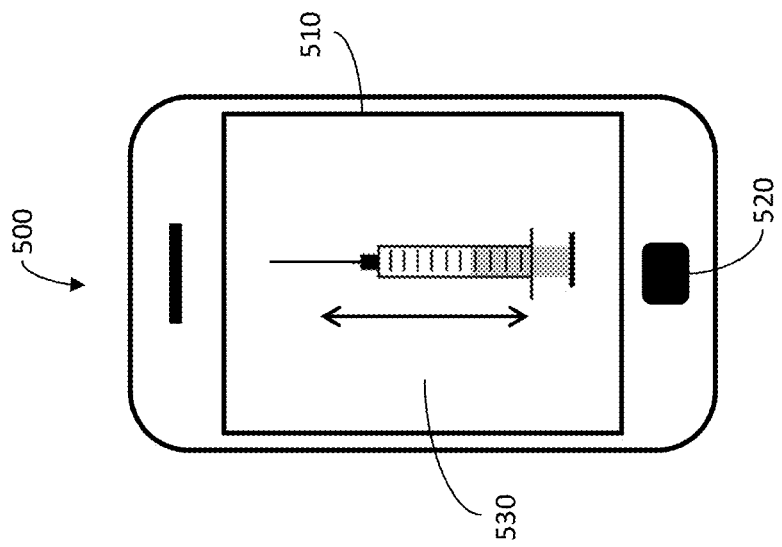
FIG. 5 is a diagram of an exemplary mobile device configured for simulated needle insertion according to some embodiments.

FIG. 5 illustrates an exemplary mobile device 500 for simulated needle insertion according to some embodiments. The mobile device 500 may include at least one processor (not shown), a display 510, at least one control 520 (which may be solely on the display 510, which may be a touch screen), and at least one first sensor (not shown). The first sensor may include an accelerometer and/or a gyroscope. Additionally, the mobile device may include at least one second sensor (not shown). The second sensor may include a magnetometer. In some embodiments, the mobile device 500 may be a smartphone. Alternatively, the mobile device 500 may be a tablet, PDA, a multimedia player, or any other suitable device.

According to some embodiments, the mobile device 500 may be configured for use as a needle simulator, as described herein. For example, the mobile device 500 may download and/or install software (e.g., an "app") that configures the mobile device for use as a needle simulator.

According to some embodiments, the mobile device 500 may present a user interface 530 representing a simulated needle on the display 510 of the mobile device 500. For example, the user interface 530 may include an image of a syringe and needle. The user interface 530 may include an indicator and control for user input representing a depth of movement of the simulated needle.

Figure 6:
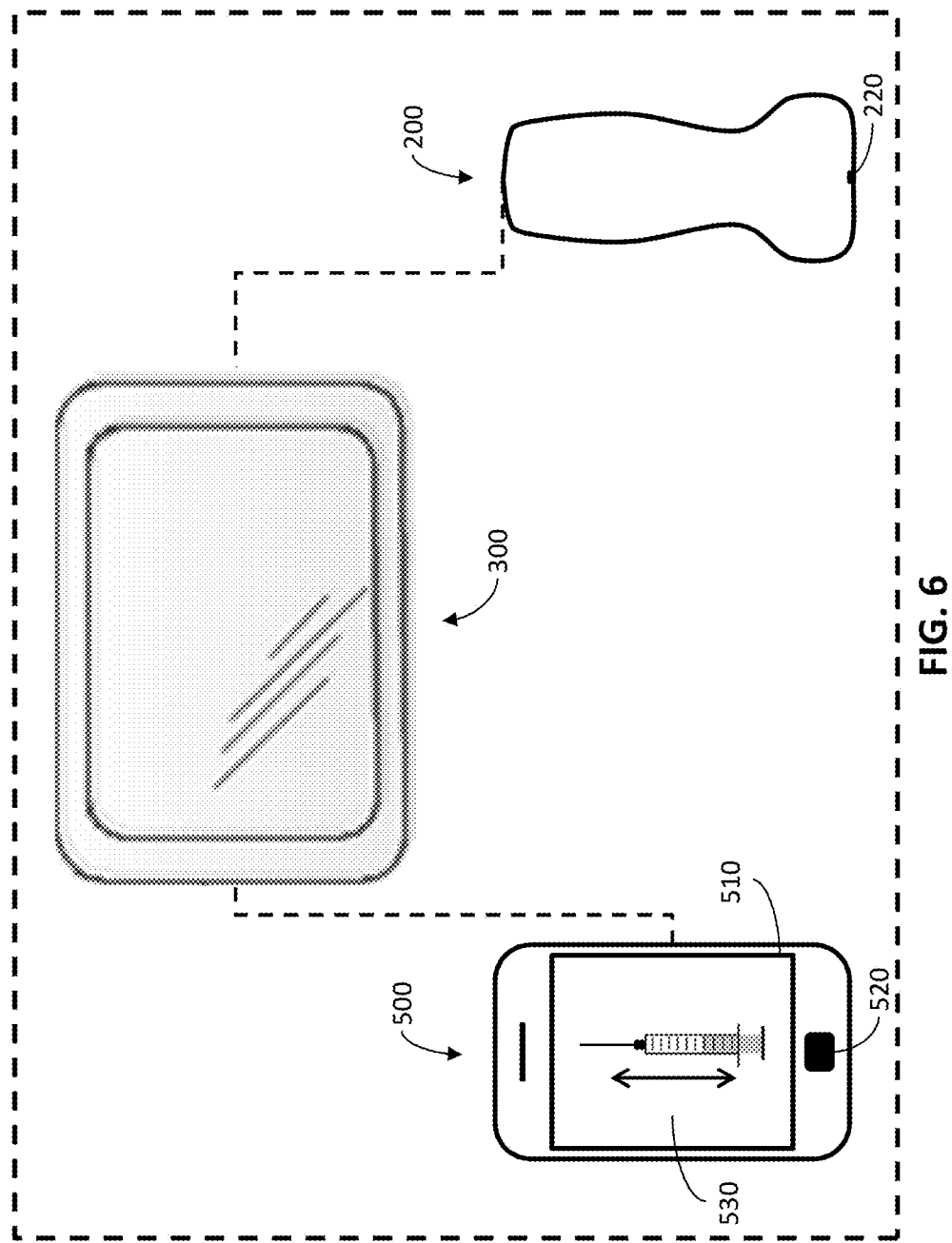
FIG. 6 is a diagram of an exemplary system for needle insertion simulation according to some embodiments.
Figure 7:
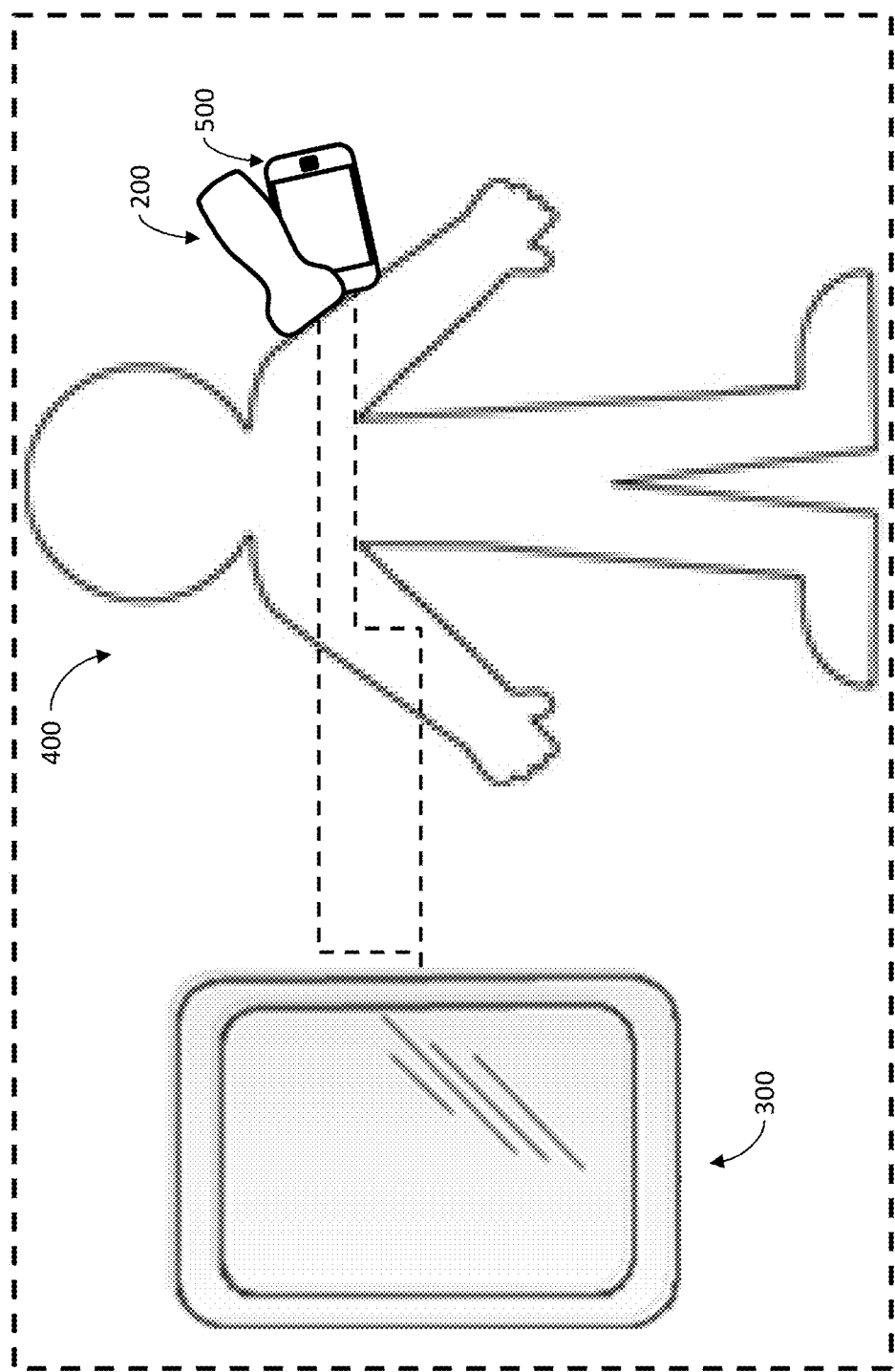
FIG. 7 is a diagram of an exemplary system for needle insertion simulation for use on a subject according to some embodiments.

According to some embodiments, the mobile device 500 may receive, from the first sensor of the mobile device 500, an orientation of the mobile device 500. For example, the processor of the mobile device 500 may read or determine the mobile device's 500 orientation by checking a reading of the first sensor. Additionally, the mobile device 500 may transmit its orientation to a second device (not shown). This transmission may be made via wired or wireless (e.g., Bluetooth) communication in any form. For example, the mobile device 500 may transmit the orientation to a computer (e.g., a computer that is connected via wires or that is within Bluetooth range). Alternatively or additionally, if the mobile device 500 has an internet connection, it may transmit the orientation to a server (not shown), and the server may relay the orientation to the second device. In some embodiments, the second device may include a display device (not shown), as illustrated in FIGS. 6 and 7. The display device may use the orientation to compute how to represent the mobile device 500 (e.g., how to display a virtual needle) in an image to be displayed, as described below.

FIG. 6 illustrates an exemplary system for needle insertion simulation according to some embodiments. In some embodiments, the system may include the mobile device 500 and the ultrasound probe 200. In some embodiments, the system may include the display device 300.

FIG. 7 illustrates an exemplary system for needle insertion simulation for use on a subject 400 according to some embodiments. In some embodiments, the system may include the mobile device 500, the ultrasound probe 200, and/or the display device 300. The following discussion may refer to FIGS. 6 and 7 jointly, with some elements not explicitly labeled in both FIGS. 6 and 7.

According to some embodiments, the mobile device 500 may present a user interface 530 representing a simulated needle on the display 510 of the mobile device 500, as discussed herein.

According to some embodiments, the mobile device 500 may receive a calibration of the first sensor of the mobile device 500 from a user control (e.g., control 520) or interface, which may be operated by the user. For example, when the user has placed the mobile device 500 at the desired position and/or orientation for the simulation, the user may trigger calibration of the first sensor of the mobile device 500 (for example, via control 520 or user interface 530). This way, the system may treat the position and/or orientation of the mobile device 500 at the time of calibration as the starting or "zero" position and/or orientation from which later movement is measured. In some embodiments, the user must maintain the starting position and only alter the orientation of the mobile device 500, which the system may assume occurs.

Alternatively, this calibration may be made unnecessary by tracking the position of the mobile device 500, which may be accomplished by tracking the position of the ultrasound probe 200 relative to the mobile device 500. According to some embodiments, the ultrasound probe 200 may receive or support the attachment of at least one tracking element 220. The tracking element 220 may be tracked by the second sensor of the mobile device 500, providing to the mobile device 500 (which may receive) the orientation and/or the position of the tracking element 220 and, thereby, the ultrasound device 200 relative to the second sensor (and thereby the mobile device 500). In some embodiments, the tracking element 220 may be a magnet, and, as discussed, the second sensor of the mobile device 500 may be a magnetometer. The magnet may be less than about five percent of the size of the ultrasound probe 200 and may be attached to the ultrasound probe 200 using a clip, tape, or any other suitable attachment mechanism. The inventors have recognized and appreciated that tracking the position and/or orientation of the ultrasound probe 200 relative to the mobile device 500 may provide more precision and realism to a simulation and potentially prevent a need for calibration of the position and/or orientation of the mobile device 500, as discussed herein. Moreover, this tracking of the ultrasound probe 200 relative to the mobile device 500 may provide a more robust tracking of the mobile device 500 than merely using the first sensor of the mobile device 500, and the user may reposition the mobile device 500 without needing to perform calibration again.

Another potential alternative to calibration may include (although calibration may be used as well), according to some embodiments, the mobile device 500 receiving, from a second sensor (not shown) of the mobile device 500, at least one image of an environment of the mobile device 500. The second sensor may include a camera, another optical sensor, or any other suitable sensor able to produce an image. The mobile device 500 may determine a position and/or an orientation of the ultrasound probe 200 and/or the subject 400 (e.g., relative to the mobile device 500) based on the image of the environment of the mobile device 500. For example, the processor of the mobile device 500 may use image processing to estimate position and/or orientation information of objects in the image.

According to some embodiments, the display device 300 may receive the orientation of the mobile device 500, as discussed above with regard to the second device. Alternatively or additionally, the display device 300 may receive the position of the mobile device 500, the position of the ultrasound probe 200, and/or the orientation of the ultrasound probe 200. The display device 300 may alternatively or additionally receive, from the mobile device 500, data indicating a relative position of the mobile device 500 and the ultrasound probe 200. For example, the display device 300 may receive, from the mobile device 500, a position and/or an orientation of the tracking element 220 attached to the ultrasound probe 200.

Alternatively, the display device 300 may receive images for display that are generated based on the position of the mobile device 500, the orientation of the mobile device 500, the position of the ultrasound probe 200, and/or the orientation of the ultrasound probe 200. For example, if the display device 300 is merely a display monitor or screen, it may only receive images or an image signal from another device.

According to some embodiments, any of the positional information (including orientation) of any components may be calculated (e.g., by the processor of the mobile device 500 or by the processor of the display device 300) based on any of the other position information given relationships. For example, the orientation of the mobile device 500 may be calculated based on (or the precision of the orientation may be improved based on) the relative orientation between the mobile device 500 and the ultrasound probe 200.

According to some embodiments, the orientation of the mobile device 500 may include three degrees of freedom, including a yaw, a pitch, and a roll of the mobile device 500. Additionally, the position of the ultrasound probe 200 (where available) may include three degrees of freedom, including an X position, a Y position, and a Z position (each corresponding to their respective axes).

According to some embodiments, the orientation of the ultrasound probe 200 may include three degrees of freedom, including a yaw, a pitch, and a roll of the ultrasound probe 200. Additionally, the position of the ultrasound probe 200 may include three degrees of freedom, including an X position, a Y position, and a Z position (each corresponding to their respective axes).

According to some embodiments, the ultrasound probe 200 may be placed on the subject 400 in order to provide the ultrasound data received by the display device 300. Additionally, the mobile device 500 may be pressed against the subject 400 (typically on the subject's skin, but clothing may also be used for a less realistic simulation) in order to prepare to simulate the ultrasound-guided needle insertion. In some embodiments, the display device 300 may show the user (not shown) where the simulated needle would be inside the subject 400 if the needle simulator were an actual needle.

According to some embodiments, the display device 300 may receive, from the ultrasound probe 200, ultrasound data. For example, as the ultrasound probe 200 scans the subject, the ultrasound probe 200 may relay ultrasound data from the scanning to the display device 300. The ultrasound data may include information needed to generate ultrasound images (and this generation of the ultrasound images may be performed by the display device 300 or by any other suitable device) for display on the display device 300.

According to some embodiments, the ultrasound images may be or at least include live ultrasound images, as discussed herein. Alternatively or additionally, the ultrasound images may be or at least include prerecorded ultrasound images. The advantages of both of these are discussed herein.

According to some embodiments, the display device 300 may receive, from a camera, at least one original ultrasound image captured by the camera. For example, if the ultrasound images (whether prerecorded or live) are not easily accessible to the display device 300 (or for any other reason), a camera may be used to record the ultrasound images from an actual display that is displaying them, such as a ultrasound system manufacturer's standard monitor (or other pre-existing display). Then, the captured ultrasound images may be used and/or modified in ways similar to those described with respect to other ultrasound images herein. For example, as described below, the ultrasound images may be displayed on the display device 300 based on the original ultrasound image(s). In some embodiments, the camera may include a "webcam," a camera module of the display device 300 (such as a built-in or attachable camera), an analog camera, or any other suitable optical device. Alternatively, original ultrasound image(s) may be captured using a video capture device (not shown) that may be connected to the actual display, such as via an external display pot like HDMI or VGA.

According to some embodiments, the display device 300 may include a user interface via which the display device 300 may receive a second user input. The display device 300 may then define, based on the second user input, an area of capture for the camera. For example, if the camera is positioned, zoomed, or focused such that the camera captures objects that are not relevant to the ultrasound images, such as background environment (e.g., curtains, walls, and so on) outside of a manufacturer's standard monitor, the user may input bounds to the area of capture so that only the desired area is provided to the display device 300. Additional processing, such as displaying an overlay, may be limited to this bounded or cropped area of the images. In some embodiments, the display device 300 may receive input via a mouse, a keyboard, and/or a touch pad that defines the area of capture using one or more single-point operations, a dragging operation, or any other suitable operation.

According to some embodiments, the camera may be mounted on the actual display. For example, the camera may be attached to the actual display using a clip, temporary adhesive, suction, or any other suitable mounting mechanism or technique. In some embodiments, the angle of the camera relative to the actual display may be fixed so that they are parallel. Alternatively, the angle may be adjustable.

Alternatively, the display device 300 may be the actual display (e.g., the manufacturer's standard monitor), and the system may interface directly with the display device 300 and/or components provided images to the display device 300. For example, native or modified code within the manufacturer's equipment could be used to manipulate ultrasound images for the additional processing described herein, such as displaying an overlay.

According to some embodiments, the mobile device 500 may receive, via the user interface 530, a user input representing a depth of movement of the simulated needle. The user input may be a sliding user input. For example, the user may swipe (on, e.g., the touch screen of the mobile device 500) from the back of a representation of a needle to the front on the user interface 530 to simulate a needle insertion. Additionally, the mobile device may transmit the user input to the second device, which may be the display device 300.

According to some embodiments, the display device 300 may display, based on the ultrasound data, one or more ultrasound images. Additionally, the ultrasound images may include an overlay (e.g., the display device 300 may display the overlay on top of or otherwise in combination with the ultrasound images). The overlay may indicate, in real-time, the orientation of the mobile device 500. For example, the display device 300 may compute, based on the orientation of the mobile device 500, an orientation of the simulated needle, and the overlay may indicate the orientation of the simulated needle, thereby indicating the orientation of the mobile device 500. Alternatively or additionally, the overlay may indicate information relating the mobile device 500 with the ultrasound probe 200. For example, the overlay may include a representation or depiction of the simulated needle (which may be similar to or different from the simulated needle displayed on the mobile device 500). The representation of the simulated needle may be positioned and oriented in the images such that, as the user moves the mobile device 500, the representation moves accordingly within the images. The overlay may be stored for repeat use, or the overlay may be generated based on information received from the mobile device 500.

According to some embodiments, the overlay may indicate, in real-time, the user input received from the mobile device 500. For example, when the user performs a sliding user input to simulate needle insertion (e.g., by swiping up on the user interface 530), the user input may be transmitted to the display device 300 and indicated by the overlay, such as by displaying an extending of the representation of the simulated needle to represent a needle extending from a syringe.

According to some embodiments, the overlay may indicate, in real-time, the position of the tracking element 220 (and thereby of the ultrasound probe 200) and/or the orientation of the tracking element 220 (and thereby of the ultrasound probe 200). For example, if the ultrasound images displayed are prerecorded, showing positional information relating to the tracking element 220 (and thereby the ultrasound probe 200) may be useful because the ultrasound images may not change as a result of moving the ultrasound probe 200. However, even prerecorded images may change if they were taken or generated from different perspectives. In some embodiments, for example, the display device 300 may compute or alter ultrasound images for display based on prerecorded ultrasound images and an orientation and/or position of the ultrasound probe 200. Alternatively or additionally, the display device 300 may select portions of prerecorded ultrasound images based on the orientation and/or position of the ultrasound probe 200.

As discussed above, it should be appreciated that embodiments and techniques herein may alternatively or additionally be used for any other invasive procedure inside a subject 400. For example, according to some embodiments, the display device 300 may receive information from a mobile device 500 configured with an application to simulate a medical tool and to transmit orientation information. Additionally, the display device 300 may receive ultrasound image data (or any other suitable data) from an ultrasound probe 200. Additionally, the display device 300 may compute an image of an object (e.g., subject 400) with an image of a simulation oriented relative to the object based on the received information. In some embodiments, computing the image may be based on an assumption that the mobile device 500 has a known position relative to the ultrasound probe 200. For example, by assuming that the mobile device 500 has a known position relative to the ultrasound probe 200, computing the image may be shorter than alternative embodiments, where the relative positions of the ultrasound probe 200 and the mobile device 500 within the same frame of reference may be used to position the image of the simulation relative to the image of the object.

Figure 10:
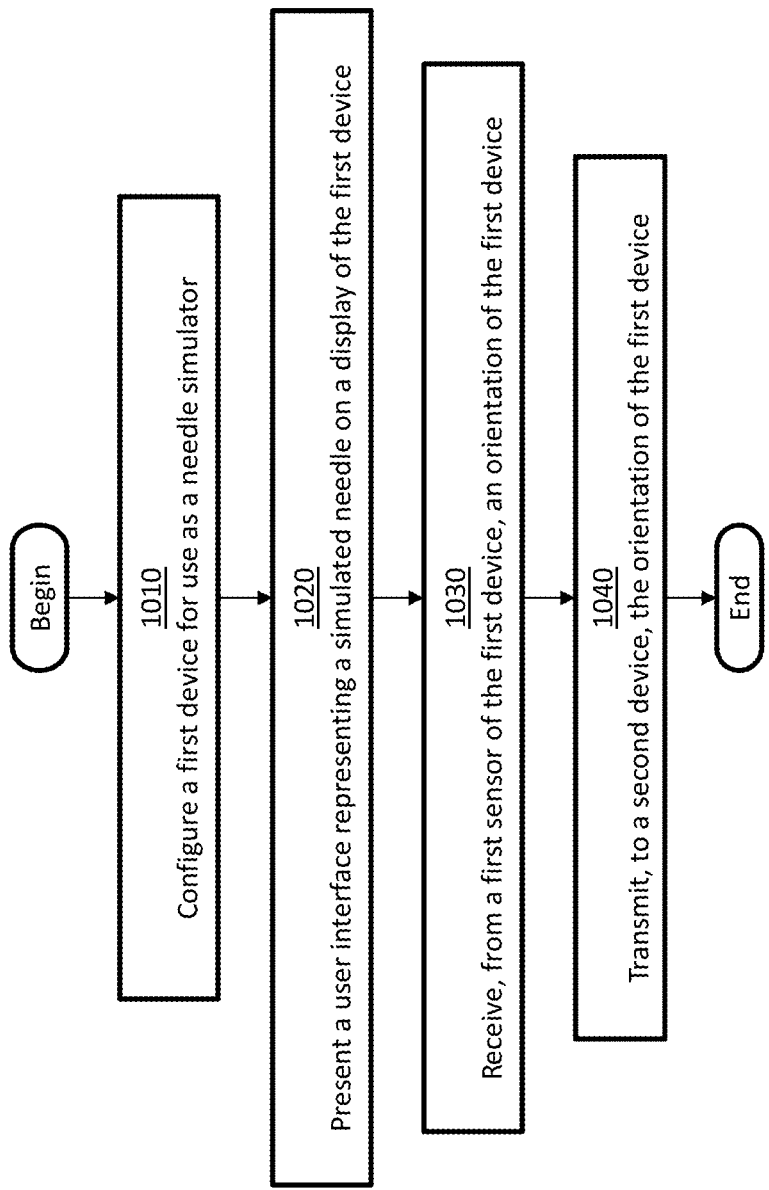
FIG. 10 is a flowchart of a method for simulating needle insertion according to some embodiments.

It should be appreciated from the foregoing that some embodiments are directed to a method for simulating needle insertion, as illustrated in FIG. 10. The method may be performed by at least one processor caused to do so by executing instructions encoded on at least one computer-readable storage medium. The method begins at act 1010, at which a first device (e.g., the mobile device 500) may be configured for use as a needle simulator. The method then proceeds to act 1020, at which a user interface representing a simulated needle on a display (e.g., display 510) of the first device may be presented.

The method proceeds then to act 1030, at which an orientation of the first device may be received from a first sensor (e.g., an accelerometer and/or gyroscope) of the first device. Then, the method proceeds to act 1040, at which the orientation of the first device may be transmitted to a second device (e.g., display device 300). The method may then end or be repeated for additional stages of a simulation or other simulations. The acts and techniques of this method are described in further detail above.

Figure 11:
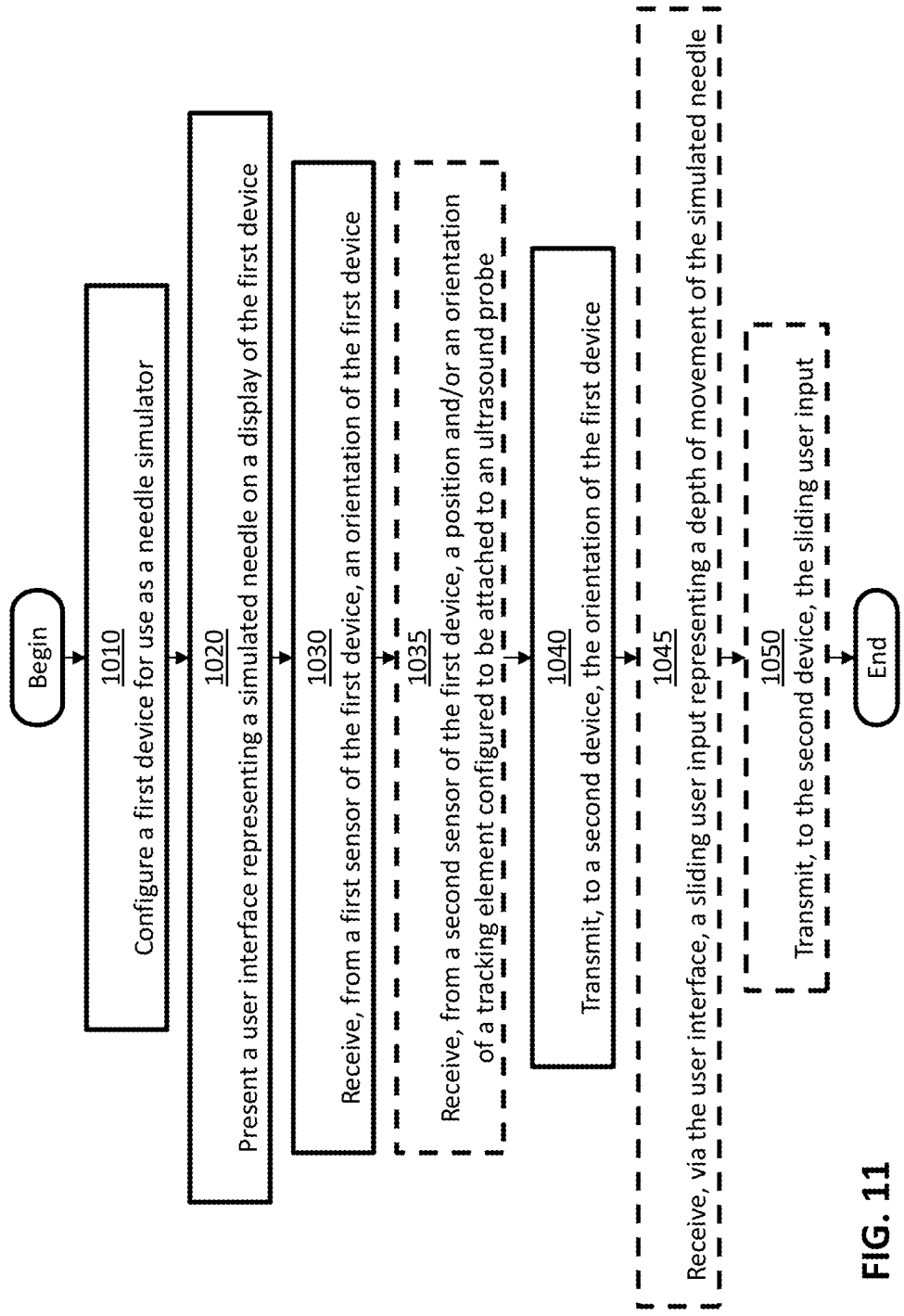
FIG. 11 is a flowchart of an additional method for simulating needle insertion according to some embodiments.

It should be appreciated from the foregoing that some embodiments are directed to an additional method for simulating needle insertion, as illustrated in FIG. 11. The method may be performed by at least one processor caused to do so by executing instructions encoded on at least one computer-readable storage medium. The method begins at act 1010 (previously described). The method then proceeds to act 1020 (previously described). The method proceeds then to act 1030 (previously described). Then, the method optionally proceeds to act 1035, at which a position and/or an orientation of a tracking element (e.g., tracking element 220) configured to be attached to an ultrasound probe (e.g., ultrasound probe 200) may be received from a second sensor (e.g., a magnetometer) of the first device.

The method proceeds then to act 1040 (previously described). Then, optionally, the method may proceed to act 1045, at which a sliding user input representing a depth of movement of the simulated needle may be received via the user interface. The method then proceeds optionally to act 1050, at which the sliding user input may be transmitted to the second device. The method may then end or be repeated for additional stages of a simulation or other simulations. The acts and techniques of this method are described in further detail above.

Figure 12:
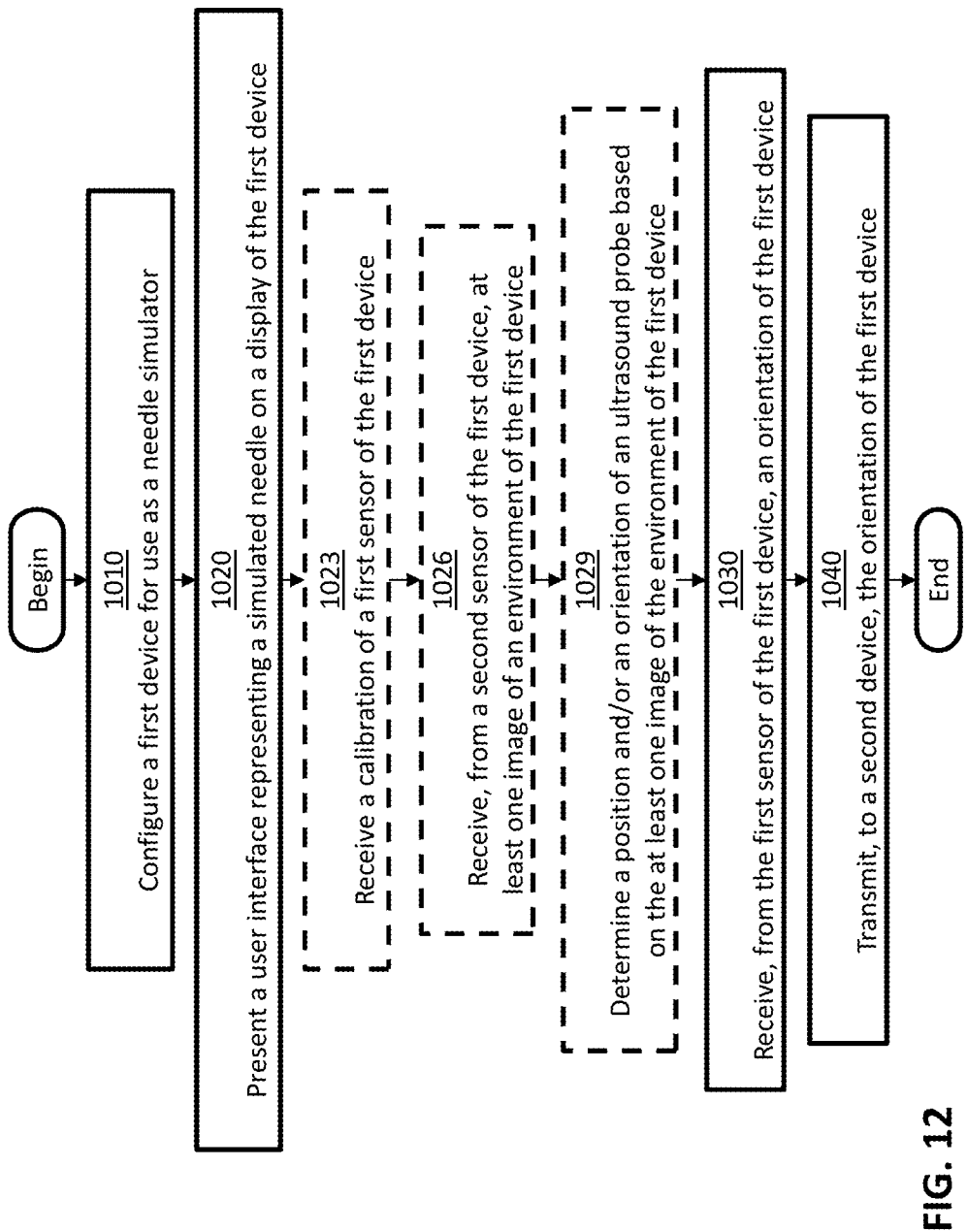
FIG. 12 is a flowchart of an alternative method for simulating needle insertion according to some embodiments.

It should be appreciated from the foregoing that some embodiments are directed to an alternative method for simulating needle insertion, as illustrated in FIG. 12. The method may be performed by at least one processor caused to do so by executing instructions encoded on at least one computer-readable storage medium. The method begins at act 1010 (previously described). The method then proceeds to act 1020 (previously described).

The method proceeds then, optionally, to act 1023, at which a calibration of the first sensor of the first device may be received. Then, the method optionally proceeds to act 1026, at which at least one image of an environment of the first device may be received from a second sensor (e.g., a camera) of the first device.

The method optionally proceeds then to act 1029, at which a position and/or an orientation of an ultrasound probe (e.g., ultrasound probe 200) based on the at least one image of the environment of the first device may be determined. Then the method proceeds to act 1030 (previously described). The method then proceeds to act 1040 (previously described). The method may then end or be repeated for additional stages of a simulation or other simulations. The acts and techniques of this method are described in further detail above.

Figure 13:
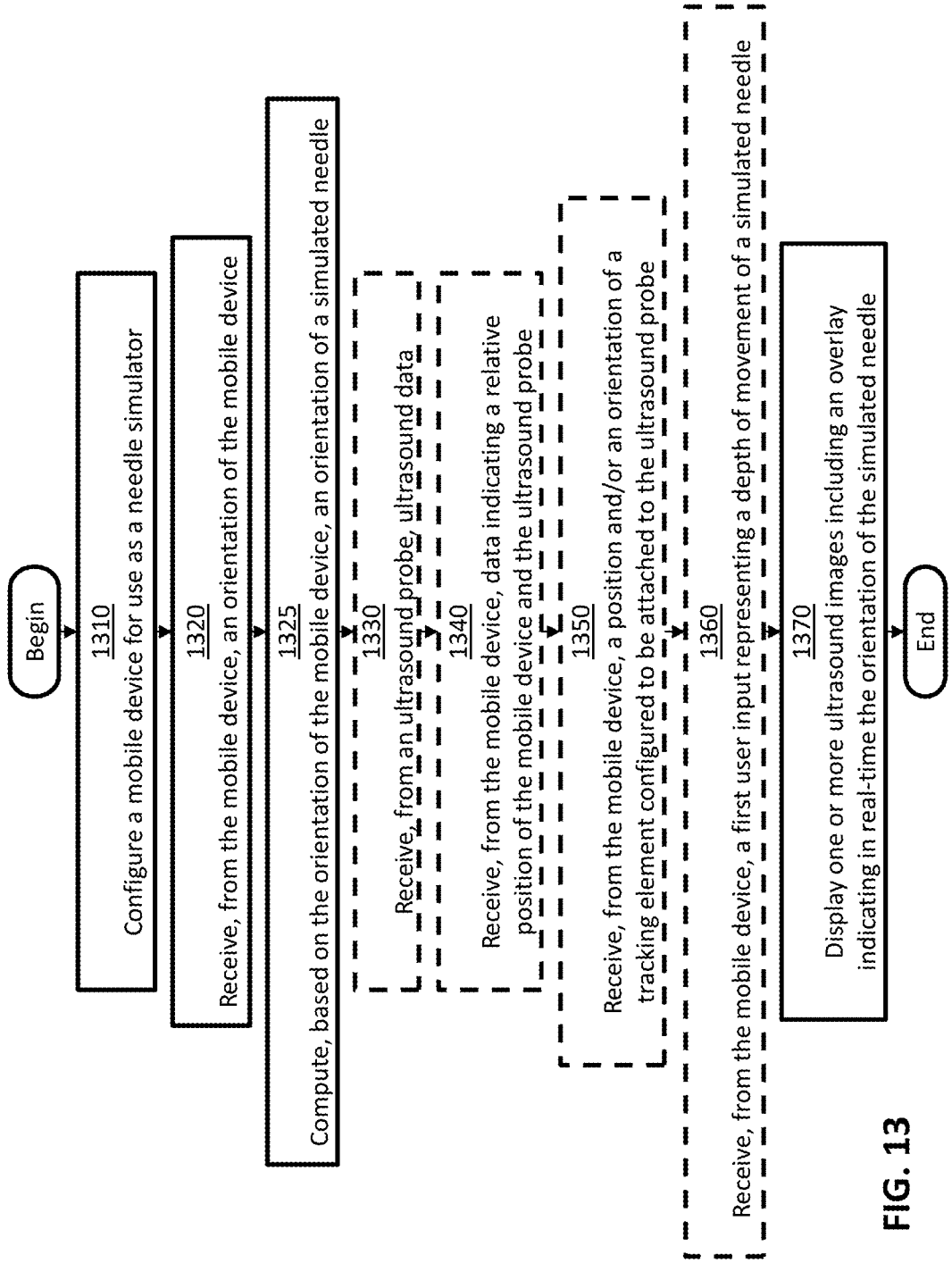
FIG. 13 is a flowchart of a method for simulating needle insertion from a display device according to some embodiments.

It should be appreciated from the foregoing that some embodiments are directed to a method for simulating needle insertion from a display device, as illustrated in FIG. 13. The method begins at act 1310, at which a mobile device (e.g., the mobile device 500) may be configured for use as a needle simulator. The method then proceeds to act 1320, at which an orientation of the mobile device may be received from the mobile device. The method then proceeds to act 1325, at which an orientation of a simulated needle may be computed based on the orientation of the mobile device.

The method optionally proceeds then to act 1330, at which ultrasound data may be received from an ultrasound probe (e.g., ultrasound probe 200). Then, the method optionally proceeds to act 1340, at which data indicating a relative position of the mobile device and an ultrasound probe may be received from the mobile device.

The method proceeds then, optionally, to act 1350, at which a position and/or an orientation of a tracking element (e.g., a magnet) configured to be attached to the ultrasound probe may be received from the mobile device. Then, optionally, the method may proceed to act 1360, at which a first user input representing a depth of movement of a simulated needle may be received from the mobile device.

The method then proceeds to act 1370, at which one or more ultrasound images including an overlay indicating in real-time the orientation of the simulated needle may be displayed. The method may then end or be repeated for additional stages of a simulation or other simulations. The acts and techniques of this method are described in further detail above.

Figure 14:
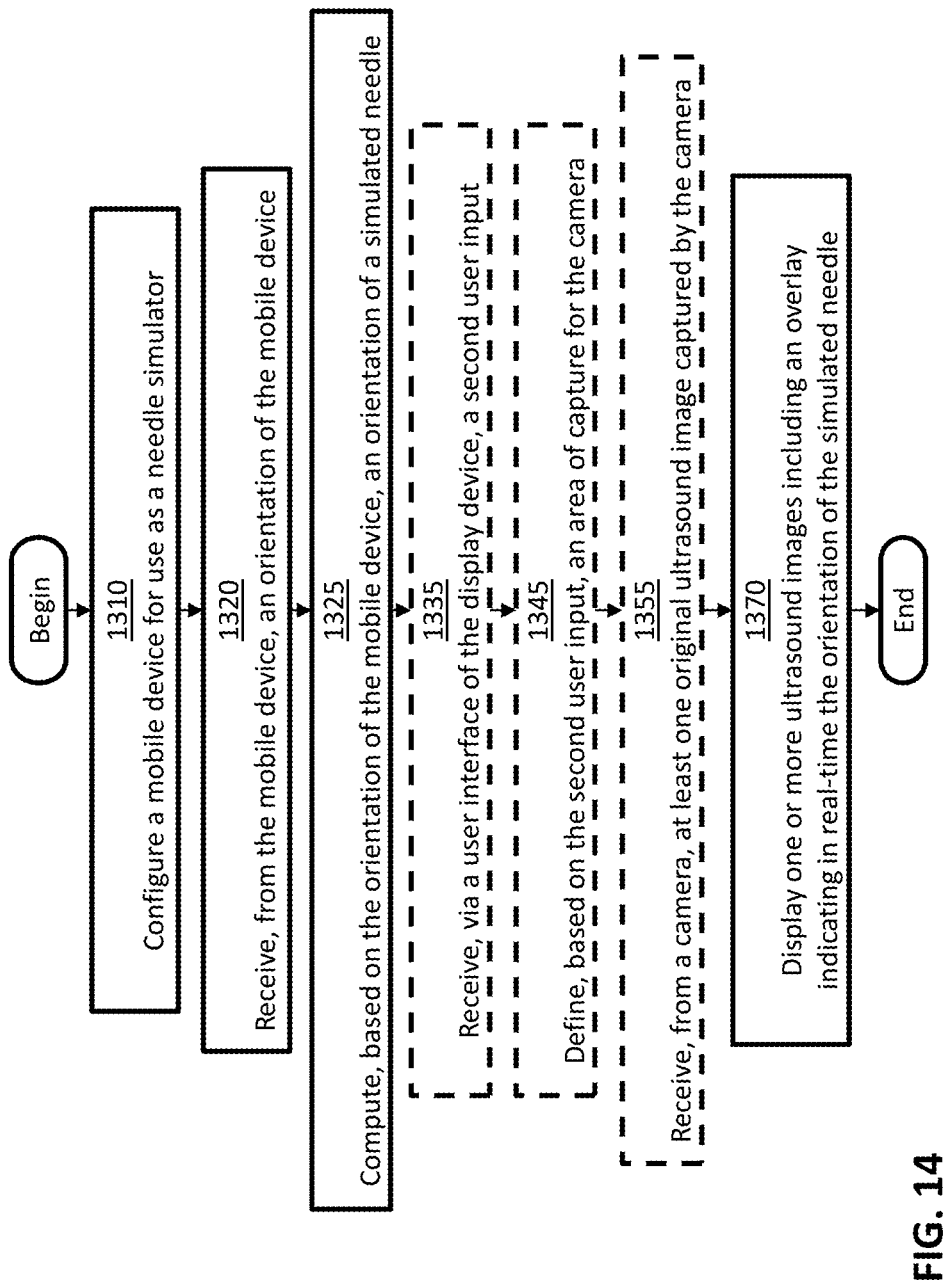
FIG. 14 is a flowchart of an alternative method for simulating needle insertion from a display device according to some embodiments.

It should be appreciated from the foregoing that some embodiments are directed to an alternative method for simulating needle insertion from a display device, as illustrated in FIG. 14. The method begins at act 1310 (previously described). The method then proceeds to act 1320 (previously described). The method then proceeds to act 1325 (previously described).

The method optionally proceeds then to act 1335, at which a second user input may be received via a user interface of a display device (e.g., display device 300). Then, the method optionally proceeds to act 1345, at which an area of capture for the camera may be defined based on the second user input.

The method proceeds then, optionally, to act 1355, at which at least one original ultrasound image captured by a camera may be received from the camera. The method then proceeds to act 1370 (previously described). The method may then end or be repeated for additional stages of a simulation or other simulations. The acts and techniques of this method are described in further detail above.

Figure 15:
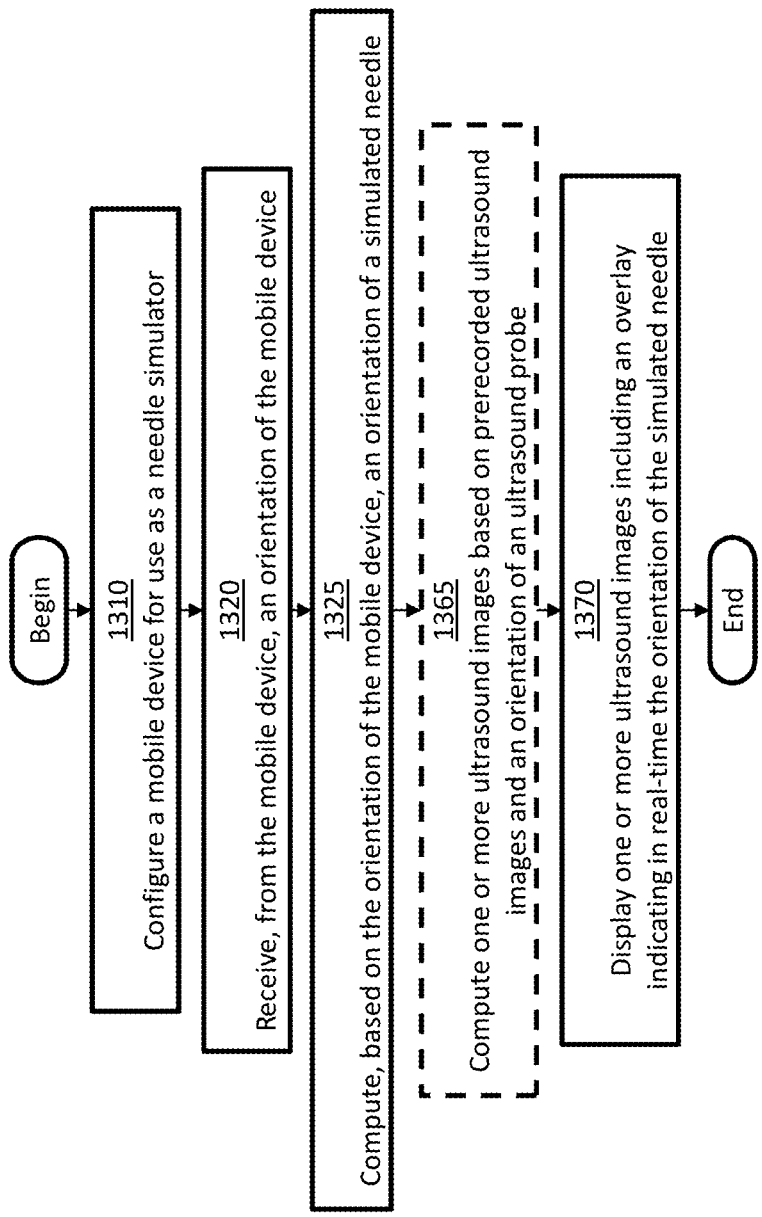
FIG. 15 is a flowchart of another alternative method for simulating needle insertion from a display device according to some embodiments.

It should be appreciated from the foregoing that some embodiments are directed to another alternative method for simulating needle insertion from a display device, as illustrated in FIG. 15. The method begins at act 1310 (previously described). The method then proceeds to act 1320 (previously described). The method optionally proceeds then to act 1365, at which one or more ultrasound images based on prerecorded ultrasound images and an orientation of an ultrasound probe (e.g., ultrasound probe 200) may be computed. The method then proceeds to act 1370 (previously described). The method may then end or be repeated for additional stages of a simulation or other simulations. The acts and techniques of this method are described in further detail above.

Figure 16:
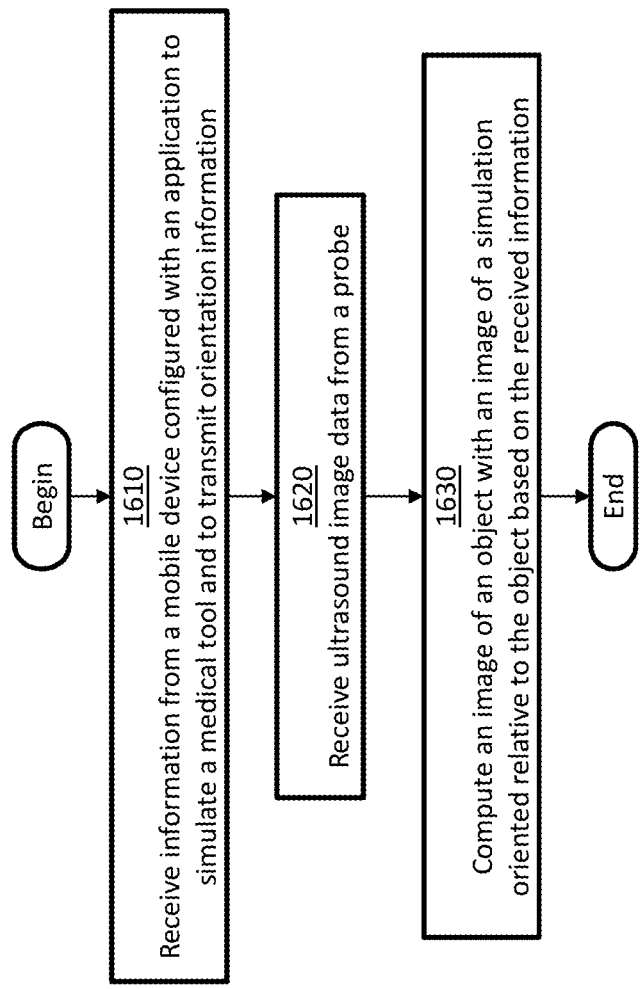
FIG. 16 is a flowchart of a method for simulating a medical procedure according to some embodiments.

It should be appreciated from the foregoing that some embodiments are directed to a method for simulating a medical procedure, as illustrated in FIG. 16. The method begins at act 1610, at which information from a mobile device configured with an application to simulate a medical tool and to transmit orientation information may be received.

The method then proceeds to act 1620, at which ultrasound image data from a probe may be received. The method proceeds then to act 1630, at which an image of an object with an image of a simulation oriented relative to the object based on the received information may be computed. The method may then end or be repeated for additional stages of a simulation or other simulations. The acts and techniques of this method are described in further detail above.

Computing Environment

Figure 17:
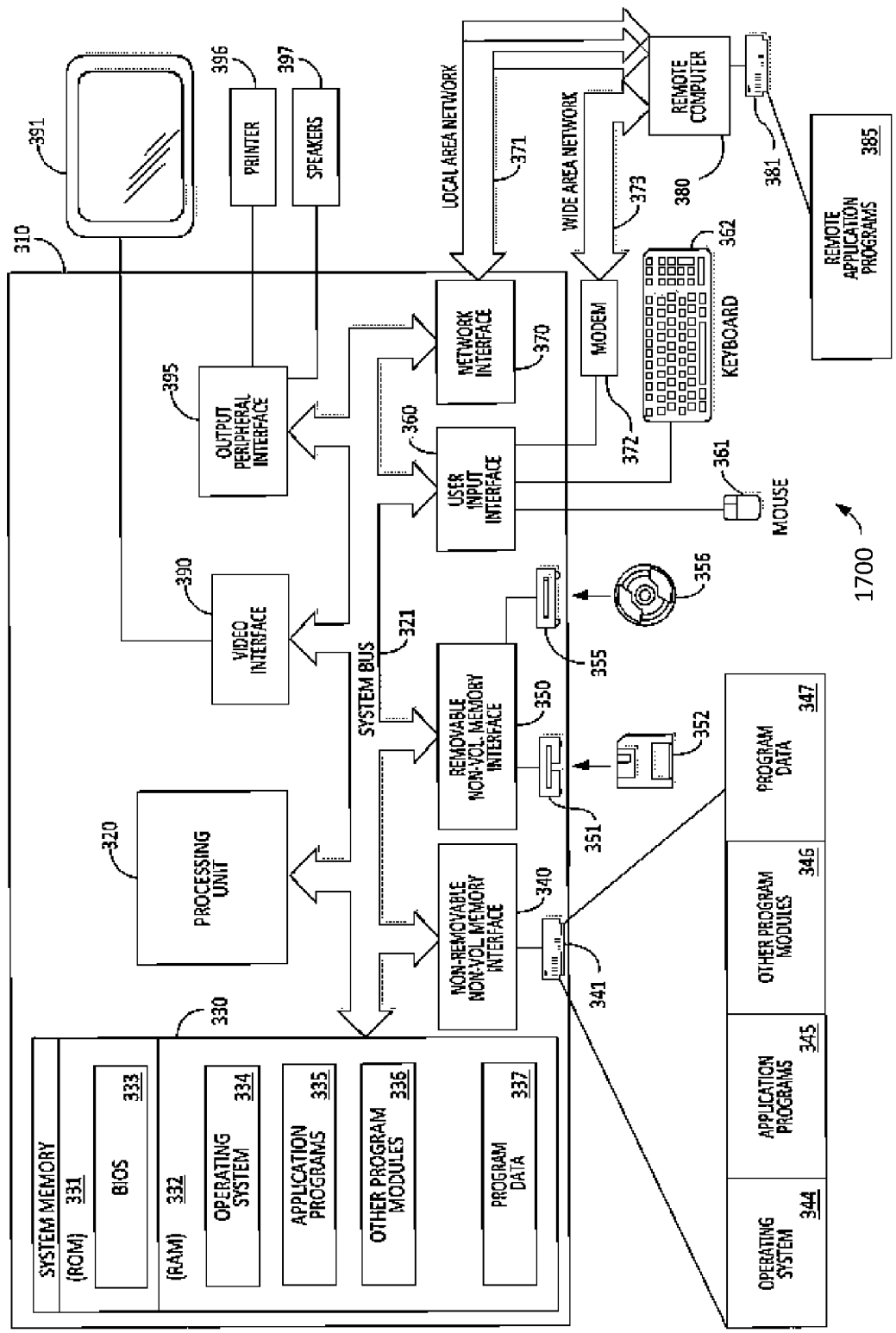
FIG. 17 is a diagram illustrating a computer system on which some embodiments may be implemented.

Techniques as described herein may be implemented on any suitable hardware, including a programmed computing system. For example, calculation of positional information of a needle simulator may be performed by programming a computing device. Similarly, manipulation of ultrasound images may be performed by a programmed computing device. FIGS. 3 through 7 illustrate components and systems that may be implemented with multiple computing devices, which may be distributed and/or centralized. Also, FIGS. 8 through 16 illustrate processes that may include algorithms executing on at least one computing device. FIG. 17 illustrates an example of a suitable computing system environment 1700 on which embodiments of these algorithms may be implemented. This computing system may be representative of a computing system that implements the techniques described herein. However, it should be appreciated that the computing system environment 1700 is only one example of a suitable computing environment and is not intended to suggest any limitation as to the scope of use or functionality of the invention. Neither should the computing environment 1700 be interpreted as having any dependency or requirement relating to any one or combination of components illustrated in the exemplary operating environment 1700.

The invention is operational with numerous other computing system environments or configurations configured to perform the functions described herein. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments or cloud-based computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 17, an exemplary system for implementing the invention includes a general purpose computing device in the form of a computer 310. Though a programmed general purpose computer is illustrated, it should be understood by one of skill in the art that algorithms may be implemented in any suitable computing device. Accordingly, techniques as described herein may be implemented in any suitable system. These techniques may be implemented in such network devices as originally manufactured or as a retrofit, such as by changing program memory devices holding programming for such network devices or software download. Thus, some or all of the components illustrated in FIG. 17, though illustrated as part of a general purpose computer, may be regarded as representing portions of a node or other component in a network system.

Components of computer 310 may include, but are not limited to, a processing unit 320, a system memory 330, and a system bus 321 that couples various system components including the system memory 330 to the processing unit 320. The system bus 321 may be any of several types of bus structures including a memory bus or memory controller, a peripheral bus, and a local bus using any of a variety of bus architectures. By way of example and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 310 typically includes a variety of computer readable media. Computer readable media can be any available media that can be accessed by computer 310 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by computer 310. Communication media typically embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example and not limitation, communication media includes wired media such as a wired network or direct-wired connection, and wireless media such as acoustic, radio frequency (RF), infrared (IR), and other wireless media. Combinations of any of the above should also be included within the scope of computer readable media.

The system memory 330 includes computer storage media in the form of volatile and/or nonvolatile memory such as read only memory (ROM) 331 and random access memory (RAM) 332. A basic input/output system 333 (BIOS), containing the basic routines that help to transfer information between elements within computer 310, such as during start-up, is typically stored in ROM 331. RAM 332 typically contains data and/or program modules that are immediately accessible to and/or presently being operated on by processing unit 320. By way of example and not limitation, FIG. 17 illustrates operating system 334, application programs 335, other program modules 336, and program data 337.

The computer 310 may also include other removable/non-removable, volatile/nonvolatile computer storage media. By way of example only, FIG. 17 illustrates a hard disk drive 341 that reads from or writes to non-removable, nonvolatile magnetic media, a magnetic disk drive 351 that reads from or writes to a removable, nonvolatile magnetic disk 352, and an optical disk drive 355 that reads from or writes to a removable, nonvolatile optical disk 356 such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 341 is typically connected to the system bus 321 through a non-removable memory interface such as interface 340, and magnetic disk drive 351 and optical disk drive 355 are typically connected to the system bus 321 by a removable memory interface, such as interface 350.

The drives and their associated computer storage media discussed above and illustrated in FIG. 17, provide storage of computer readable instructions, data structures, program modules, and other data for the computer 310. In FIG. 17, for example, hard disk drive 341 is illustrated as storing operating system 344, application programs 345, other program modules 346, and program data 347. Note that these components can either be the same as or different from operating system 334, application programs 335, other program modules 336, and program data 337. Operating system 344, application programs 345, other program modules 346, and program data 347 are given different numbers here to illustrate that, at a minimum, they are different copies. A user may enter commands and information into the computer 310 through input devices such as a keyboard 362 and pointing device 361, commonly referred to as a mouse, trackball, or touch pad. Other input devices (not shown) may include a microphone, joystick, game pad, satellite dish, scanner, or the like. These and other input devices are often connected to the processing unit 320 through a user input interface 360 that is coupled to the system bus, but may be connected by other interface and bus structures, such as a parallel port, game port, or a universal serial bus (USB). A monitor 391 or other type of display device is also connected to the system bus 321 via an interface, such as a video interface 390. In addition to the monitor, computers may also include other peripheral output devices such as speakers 397 and printer 396, which may be connected through an output peripheral interface 395.

The computer 310 may operate in a networked environment using logical connections to one or more remote computers, such as a remote computer 380. The remote computer 380 may be a personal computer, a server, a router, a network PC, a peer device, or some other common network node, and typically includes many or all of the elements described above relative to the computer 310, although only a memory storage device 381 has been illustrated in FIG. 17. The logical connections depicted in FIG. 17 include a local area network (LAN) 371 and a wide area network (WAN) 373, but may also include other networks. Such networking environments are commonplace in offices, enterprise-wide computer networks, intranets, and the Internet.

When used in a LAN networking environment, the computer 310 is connected to the LAN 371 through a network interface or adapter 370. When used in a WAN networking environment, the computer 310 typically includes a modem 372 or other means for establishing communications over the WAN 373, such as the Internet. The modem 372, which may be internal or external, may be connected to the system bus 321 via the user input interface 360, or other appropriate mechanism. In a networked environment, program modules depicted relative to the computer 310, or portions thereof, may be stored in the remote memory storage device. By way of example and not limitation, FIG. 17 illustrates remote application programs 385 as residing on memory device 381. It will be appreciated that the network connections shown are exemplary and other means of establishing a communications link between the computers may be used.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the attached claims, various elements are recited in different claims. However, the claimed elements, even if recited in separate claims, may be used together in any suitable combination.

The invention claimed is:

1. A method for simulating medical tool insertion, the method comprising:
   providing a medical tool simulator comprising a hand-held device comprising: a syringe comprising a housing having an injection end, and an elongated member representing a needle and protruding from the injection end of the syringe, and wherein the elongated member is configured to decrease the length of protrusion of the elongated member from the injection end of the syringe without penetrating a human body by retracting into the syringe when a threshold force is applied at the distal end of the elongated member that is opposite the syringe when the elongated member is fully protruding from the injection end of the syringe, and the elongated member comprising at least one first sensor configured to transmit position data of the distal end of the elongated member relative to the injection end of the syringe and configured to output information indicating flexing of the elongated member against another object;
   providing an ultrasound probe, wherein the ultrasound probe is configured to host at least one second sensor to indicate a position of the ultrasound probe, the at least one first sensor is further configured to indicate an orientation of the elongated member, and the at least one second sensor is further configured to indicate an orientation of the ultrasound probe;
   receiving, from the ultrasound probe, live ultrasound data representing a portion of the human body being imaged by the ultrasound probe in real-time;
   receiving the position data from the hand-held device;
   computing a position of the distal end of the elongated member based on the received position data while at least a portion of the elongated member is translated into the housing, wherein the computed position of the distal end of the elongated member is different from an actual position of the distal end of the elongated member; and
   generating an image of the portion of the human body with an image of a simulated medical tool positioned relative to the portion of the human body based on the computed position of the medical tool simulator, wherein the image of the portion of the human body comprises one or more live ultrasound images based on the received live ultrasound data.

2. The method of claim 1, wherein: the method further comprises receiving data from at least one third sensor indicating a relative depth of movement of the elongated member within the syringe.

3. The method of claim 2, further comprising: a display device configured to: receive the position of the distal end of the elongated member, the orientation of the elongated member, the position of the ultrasound probe, and the orientation of the ultrasound probe; receive, from the ultrasound probe, ultrasound data; and display, based on the ultrasound data, one or more ultrasound images including an overlay indicating in real-time information relating the elongated member with the ultrasound probe.

4. The method of claim 3, wherein: the display device is further configured to compute the information relating the elongated member with the ultrasound probe based on at least one of the position of the elongated member, the orientation of the elongated member, the relative depth of movement of the elongated member within the syringe, the position of the ultrasound probe, and the orientation of the ultrasound probe.

5. The method of claim 3, wherein: the one or more ultrasound images comprise live ultrasound images.

6. The method of claim 1, wherein: the at least one first sensor and the at least one second sensor comprise magnetic sensors.

7. The method of claim 1, wherein the method further comprises: receiving an orientation of the medical tool simulator, a position of the ultrasound probe, and an orientation of the ultrasound probe; and displaying, based on the live ultrasound data, the image of the portion of the human body with the image of the simulated medical tool positioned relative to the portion of the human body, the image of the simulated medical tool comprising an overlay indicating in real-time information relating the medical tool simulator with the ultrasound probe.

8. The method of claim 7, further comprising: computing the information relating the medical tool simulator with the ultrasound probe based on at least one of the position of the medical tool simulator, the orientation of the medical tool simulator, the position of the ultrasound probe, and the orientation of the ultrasound probe.

9. The method of claim 1, wherein the method further comprises: receiving an orientation of the medical tool simulator from the hand-held device, the hand-held device comprising a mobile device.

10. The method of claim 1, wherein the method further comprises: receiving information indicating a relative depth of movement of an elongated member within the housing.

11. A medical tool insertion simulation system comprising:
   a medical tool simulator comprising a hand-held device comprising: a syringe comprising a housing having an injection end, and an elongated member representing a needle and protruding from the injection end of the syringe, and wherein the elongated member is configured to decrease the length of protrusion of the elongated member from the injection end of the syringe without penetrating a human body by retracting into the syringe when a threshold force is applied at the distal end of the elongated member that is opposite the syringe when the elongated member is fully protruding from the injection end of the syringe, and the elongated member comprising at least one first sensor configured to transmit position data of the distal end of the elongated member relative to the injection end of the syringe and configured to output information indicating flexing of the elongated member against another object;

an ultrasound probe hosting at least one second sensor, wherein the at least one first sensor and/or the at least one second sensor is configured to indicate a relative position between the medical tool simulator and the ultrasound probe;

at least one processor; and at least one non-transitory computer-readable storage medium encoded with executable instructions that, when executed by the at least one processor, cause the at least one processor to perform a method for simulating medical tool insertion, the method comprising:

receiving, from the ultrasound probe, live ultrasound data representing a portion of a human body being imaged by the ultrasound probe in real-time;

receiving the position data from the hand-held device;

computing a position of the distal end of the elongated member based on the received position data while at least a portion of the elongated member is translated into the housing, wherein the computed position is different from an actual position of the distal end of the elongated member; and generating an image of the portion of the human body with an image of a simulated medical tool positioned relative to the portion of the human body based on the computed position of the medical tool simulator, wherein the image of the portion of the human body comprises one or more live ultrasound images based on the received live ultrasound data.

12. The medical tool insertion simulation system of claim 11, wherein:

the at least one first sensor and/or the at least one second sensor is further configured to indicate a relative orientation between the medical tool simulator and the ultrasound probe.

13. The medical tool insertion simulation system of claim 12, wherein: the medical tool simulator and/or the elongated member comprises at least one third sensor configured to indicate a relative depth of movement of the elongated member within the housing.

14. The medical tool insertion simulation system of claim 12, further comprising:

a display device configured to:

receive the relative position of the medical tool simulator and the ultrasound probe and the relative orientation of the medical tool simulator and the ultrasound probe;

receive, from the ultrasound probe, ultrasound data; and display, based on the ultrasound data, one or more ultrasound images including an overlay indicating in real-time information relating the medical tool simulator with the ultrasound probe.

15. The medical tool insertion simulation system of claim 11, wherein:

the at least one first sensor and the at least one second sensor comprise magnetic sensors, capacitive sensors, or potentiometers.

* * * * *